(12) United States Patent
Maeno et al.

(10) Patent No.: US 10,485,455 B2
(45) Date of Patent: Nov. 26, 2019

(54) ESTIMATION DEVICE, VIBRATION STATE ESTIMATION METHOD, AND RECORDING MEDIUM

(71) Applicant: Oki Electric Industry Co., Ltd., Tokyo (JP)

(72) Inventors: Kurato Maeno, Tokyo (JP); Kohei Yamamoto, Tokyo (JP)

(73) Assignee: Oki Electric Industry Co., Ltd., Tokyo (JP)

( * ) Notice: Subject to any disclaimer, the term of this patent is extended or adjusted under 35 U.S.C. 154(b) by 988 days.

(21) Appl. No.: 14/996,200

(22) Filed: Jan. 14, 2016

(65) Prior Publication Data

US 2016/0310044 A1 Oct. 27, 2016

(30) Foreign Application Priority Data

Apr. 23, 2015 (JP) ................................ 2015-088587

(51) Int. Cl.

| A61B 5/113 | (2006.01) |
| A61B 5/11 | (2006.01) |
| A61B 8/08 | (2006.01) |
| A61B 7/00 | (2006.01) |
| A61B 5/00 | (2006.01) |

(52) U.S. Cl.
CPC ............ *A61B 5/113* (2013.01); *A61B 5/7221* (2013.01); *A61B 7/003* (2013.01); *A61B 8/488* (2013.01)

(58) Field of Classification Search
CPC ...... A61B 5/113; A61B 5/0507; A61B 5/7221; A61B 8/08; A61B 7/003; A61B 8/488
See application file for complete search history.

(56) References Cited

U.S. PATENT DOCUMENTS

| 2006/0009704 A1* | 1/2006 | Okada ................. A61B 5/1135 600/529 |
| 2008/0074307 A1* | 3/2008 | Boric-Lubecke .... A61B 5/0205 342/28 |
| 2012/0116186 A1* | 5/2012 | Shrivastav ........... A61B 5/0507 600/301 |

FOREIGN PATENT DOCUMENTS

| JP | 2006-263032 A | 10/2006 |
| JP | 2014-014708 A | 1/2014 |

OTHER PUBLICATIONS

English Translation of Detailed Description of JP2014-014708.*

* cited by examiner

*Primary Examiner* — Regis J Betsch
*Assistant Examiner* — Jeremy A Delozier
(74) *Attorney, Agent, or Firm* — Rabin & Berdo, P.C.

(57) ABSTRACT

An estimation device includes a first converting unit configured to convert a beat signal to a one-dimensional first candidate signal on the basis of a two-dimensional distribution of the beat signal, a second converting unit configured to convert the beat signal to a one-dimensional second candidate signal on the basis of a two-dimensional position change of the beat signal, and a signal deciding unit configured to decide a one-dimensional signal on the basis of the first candidate signal and the second candidate signal.

12 Claims, 11 Drawing Sheets

ESTIMATION DEVICE, VIBRATION STATE ESTIMATION METHOD, AND RECORDING MEDIUM

CROSS REFERENCE TO RELATED APPLICATION(S)

This application is based upon and claims benefit of priority from Japanese Patent Application No. 2015-088587, filed on Apr. 23, 2015, the entire contents of which are incorporated herein by reference.

BACKGROUND

The present invention relates to an estimation device, an estimation method, and a recording medium.

In recent years, there has been developed a technology that detects vibration such as respiration of a subject in a contactless manner and estimates the detected vibration state in order to determine a health state of the subject. For example, JP 2006-263032A discloses a means for measuring vibration of a subject via an air pad equipped in the bedding used by the subject and calculating a cycle of the vibration of the subject from the measured signal. Also, JP 2014-014708A discloses a technology that calculates a cycle of vibration by identifying a boundary of a waveform of each one cycle of the vibration from a norm of a signal on a two-dimensional plane which is referred to as an IQ plane, with respect to an IQ signal (I: In-phase, Q: Quadrature-phase) indicating vibration of a subject acquired by a Doppler sensor.

SUMMARY

However, in above JP 2006-263032A, a fine fluctuation included in a vibration waveform is decreased by a low-pass filter, and therefore the waveform of the vibration including the fine fluctuation is not extracted accurately, and the cycle of the vibration is not estimated accurately. Also, in above JP 2014-014708A, when noise is superposed on an IQ signal indicating vibration, or when vibration is generated continuously in a seamless manner, a vibration stop interval that breaks a cycle of vibration is less likely to be detected, so as to make it difficult to estimate the cycle of the vibration.

Thus, the present invention is made in consideration of the above problem, and a purpose of the present invention is to provide a novel and improved estimation device capable of accurately extracting a waveform of vibration for estimating a cycle of the vibration.

According to an embodiment of the present invention, there is provided an estimation device including a first converting unit configured to convert a beat signal to a one-dimensional first candidate signal on the basis of a two-dimensional distribution of the beat signal; a second converting unit configured to convert the beat signal to a one-dimensional second candidate signal on the basis of a two-dimensional position change of the beat signal; and a signal deciding unit configured to decide a one-dimensional signal on the basis of the first candidate signal and the second candidate signal.

The above signal deciding unit may select at least any one of the first candidate signal or the second candidate signal on the basis of an evaluation value decided by comparing a feature value of the first candidate signal and a feature value of the second candidate signal.

The above signal deciding unit may decide the evaluation value by comparing a frequency of the first candidate signal and a frequency of the second candidate signal.

The above signal deciding unit may select at least any one of the first candidate signal or the second candidate signal on the basis of an evaluation value decided according to an amount of change of a rotation angle of the beat signal with respect to a center of a distribution estimated on the basis of the distribution on a two-dimensional plane of the beat signal before converting.

When selecting both of the first candidate signal and the second candidate signal, the above signal deciding unit may decide the one-dimensional signal by weighting the first candidate signal and the second candidate signal using the evaluation value.

When selecting a candidate signal different from one of the first candidate signal and the second candidate signal which was selected at the last time, or when selecting both of the first candidate signal and the second candidate signal, the above signal deciding unit may adjust a phase of one of the first candidate signal or the second candidate signal, to a phase of the other of the first candidate signal or the second candidate signal.

The above first converting unit may convert the beat signal to the first candidate signal, by calculating an inner product of a two-dimensional vector expressing the beat signal and an eigenvector corresponding to a maximum eigenvalue for a covariance matrix of the beat signal.

The above second converting unit may convert the beat signal to the second candidate signal, by calculating a product of a distance from a center of a distribution estimated on the basis of the distribution on a two-dimensional plane of the beat signal to a position of the beat signal and an amount of change of a rotation angle of the beat signal with respect to the center.

Also, the above estimation device may further include a frequency estimating unit configured to estimate a frequency of the one-dimensional signal decided by the signal deciding unit, a reference position estimating unit configured to estimate a reference position of the one-dimensional signal on the basis of the frequency estimated by the frequency estimating unit, and a cycle calculating unit configured to calculate an interval between one reference position estimated by the reference position estimating unit and another reference position next to it, as a cycle of the one-dimensional signal.

The above beat signal may be a beat signal detected by a Doppler sensor in response to vibration caused by respiration of a living body.

According to another embodiment of the present invention, there is provided an estimation method including: a step for converting a beat signal to a one-dimensional first candidate signal on the basis of a distribution of the beat signal on a two-dimensional plane; a step for converting the beat signal to a one-dimensional second candidate signal on the basis of a temporal change of a position on a two-dimensional plane of the beat signal; and a step for deciding a one-dimensional signal by selecting at least any one of the first candidate signal and the second candidate signal on the basis of the converted first candidate signal and the converted second candidate signal.

According to another embodiment of the present invention, there is provided a non-transitory computer readable recording medium including instructions for execution by a control portion of an estimation device, the instructions including: converting a beat signal to a one-dimensional first candidate signal on the basis of a two-dimensional distribution of the beat signal; converting the beat signal to a one-dimensional second candidate signal on the basis of a two-dimensional position change of the beat signal; and deciding a one-dimensional signal on the basis of the first candidate signal and the second candidate signal.

As described above, the present invention can accurately extract a waveform of vibration for estimating a cycle of the vibration.

DETAILED DESCRIPTION OF THE EMBODIMENT(S)

Figure 1:
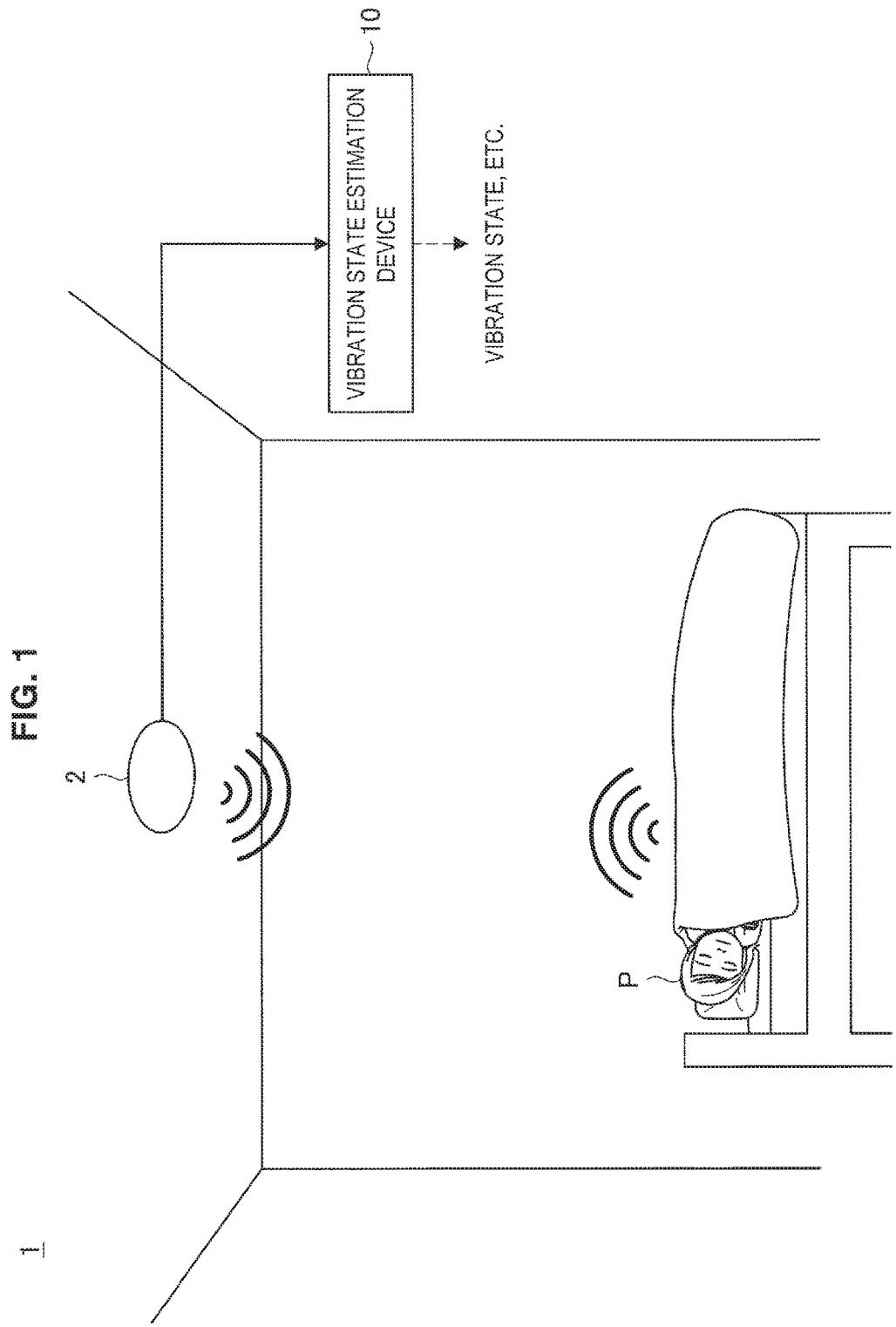
FIG. 1 is a diagram illustrating an overview of a vibration state estimation system according to an embodiment of the present invention.

Hereinafter, referring to the appended drawings, preferred embodiments of the present invention will be described in detail. It should be noted that, in this specification and the appended drawings, structural elements that have substantially the same function and structure are denoted with the same reference numerals, and repeated explanation thereof is omitted.

<1. Exemplary Configuration of Vibration State Estimation System>

FIG. 1 is a diagram illustrating an overview of a vibration state estimation system 1 according to an embodiment of the present invention. Referring to FIG. 1, the vibration state estimation system 1 includes a Doppler sensor 2 and a vibration state estimation device 10.

As illustrated in FIG. 1, the Doppler sensor 2 is installed on a ceiling or the like of a room for example, and radiates a radiation wave such as light, electromagnetic wave, or sound wave, toward the inside of the room which is a detection area, and receives a reflected wave reflected by an object (for example, a person P in FIG. 1). In this case, the frequency of the reflected wave changes from the frequency of the radiation wave by Doppler effect generated by a motion such as vibration of the object. The Doppler sensor 2 generates a beat signal having a differential frequency between the frequency of the radiation wave and the frequency of the reflected wave. The Doppler sensor 2 may employ a quadrature detection method, and in that case the Doppler sensor 2 generates two types of beat signals including a cosine wave component (I component) and a sine wave component (Q component). The Doppler sensor 2 outputs the generated beat signal to the vibration state estimation device 10.

Note that the Doppler sensor 2 can be installed at any position where the vibration of the object is detectable. Although in the example illustrated in FIG. 1 the Doppler sensor 2 is configured with a radiation wave transmitter unit and a reflected wave receiver unit integrally, the Doppler sensor 2 may be configured such that the transmitter unit and the receiver unit are separated from each other. Also, the radiation wave radiated by the Doppler sensor 2 may be a wave of any frequency band that generates Doppler effect because of the vibration of the object. For example, when the Doppler sensor senses vibration of respiration, a wave whose wavelength is larger as compared with the displacement of the vibration of respiration, such as 2.4 GHz to 10.5 GHz band, is used in many cases. However, in the present embodiment, it is preferable that a wave of a band of quasi millimeter wave or millimeter wave, such as 24 GHz band, be used for a wide displacement of the vibration of the respiration, in order to detect fine fluctuation included in the waveform.

The vibration state estimation device 10, which is an example of the estimation device, is a device that estimates a vibration state of a subject (for example, a person P) on the basis of a beat signal output from the Doppler sensor 2. The vibration state estimation device 10 may be configured with one or a plurality of information processing devices on a network, for example. More specifically, the vibration state estimation device 10 may be configured with a server, a personal computer (PC), or the like. Here, in the present specification, the vibration state means an amplitude or a cycle obtained from a vibration waveform of the object, for example. For example, the vibration state estimation device 10 is capable of estimating a vibration state of the person P on the basis of a beat signal obtained from vibration such as respiration of the person P. The vibration state estimation device 10 is capable of transmitting the estimated vibration state to an external device or the like by wire or wirelessly via a communication unit (not depicted), for example. Thereby, for example, the external device can perform analysis with respect to the vibration state. The vibration state is analyzed to check the health state of the person P or the like, for example. Note that the analysis of the vibration state may be performed not by the aforementioned external device, but by the main body of the vibration state estimation device 10.

Here, the beat signal obtained from the vibration of the person P can include signals resulting from various motions of the person P. For example, the beat signal can include not only the vibration of the respiration of the person P, but also the vibration such as body motion and heartbeat of the person P. Further, the beat signal generated by the Doppler sensor 2 can include noise from the surrounding environment. Hence, for example, when the vibration of the respiration is to be detected, it is desirable to detect only respiration waveform information from the beat signal.

For example, in JP 2006-263032A, a filter process by a bandpass filter of 0.15 to 0.30 Hz that corresponds to the frequency band of respiration is performed for the vibration signal to detect the cycle of the respiration. However, in that case, when fine fluctuation is generated for each respiration cycle, the fluctuation is reduced by the bandpass filter, and therefore it is difficult to extract a waveform that indicates vibration accompanying the fine fluctuation. Also, when the technology disclosed in the above patent document is applied to the beat signal, a high-frequency component is superposed on the vibration waveform, depending on the magnitude of the amplitude of the vibration, as the detail thereof is described later. In this case, a waveform including a plurality of peaks is extracted in one cycle of respiration, and therefore it is possible to estimate the cycle of vibration of the respiration erroneously.

Also, in JP 2014-014708 A, the cycle of the respiration is estimated by calculating a norm of the beat signal on the IQ plane and detecting the time point at which the norm is substantially zero as a switch time between inhale and exhale of the respiration. However, for example, when much noise is superposed on the beat signal, or when the motion of the respiration is seamless and continuous, it is difficult to detect the time point at which the norm is substantially zero. Hence, it is possible to estimate the cycle of the respiration erroneously.

Thus, in view of the above circumstances, the vibration state estimation device 10 has been created. The vibration state estimation device 10 according to an embodiment of the present invention is capable of accurately extracting the waveform of the vibration for estimating the cycle of the vibration, such as respiration, for example. In the following, the configuration of the vibration state estimation device 10 according to an embodiment will be described in more detail.

<2. Exemplary Configuration of Vibration State Estimation Device>

Figure 2:
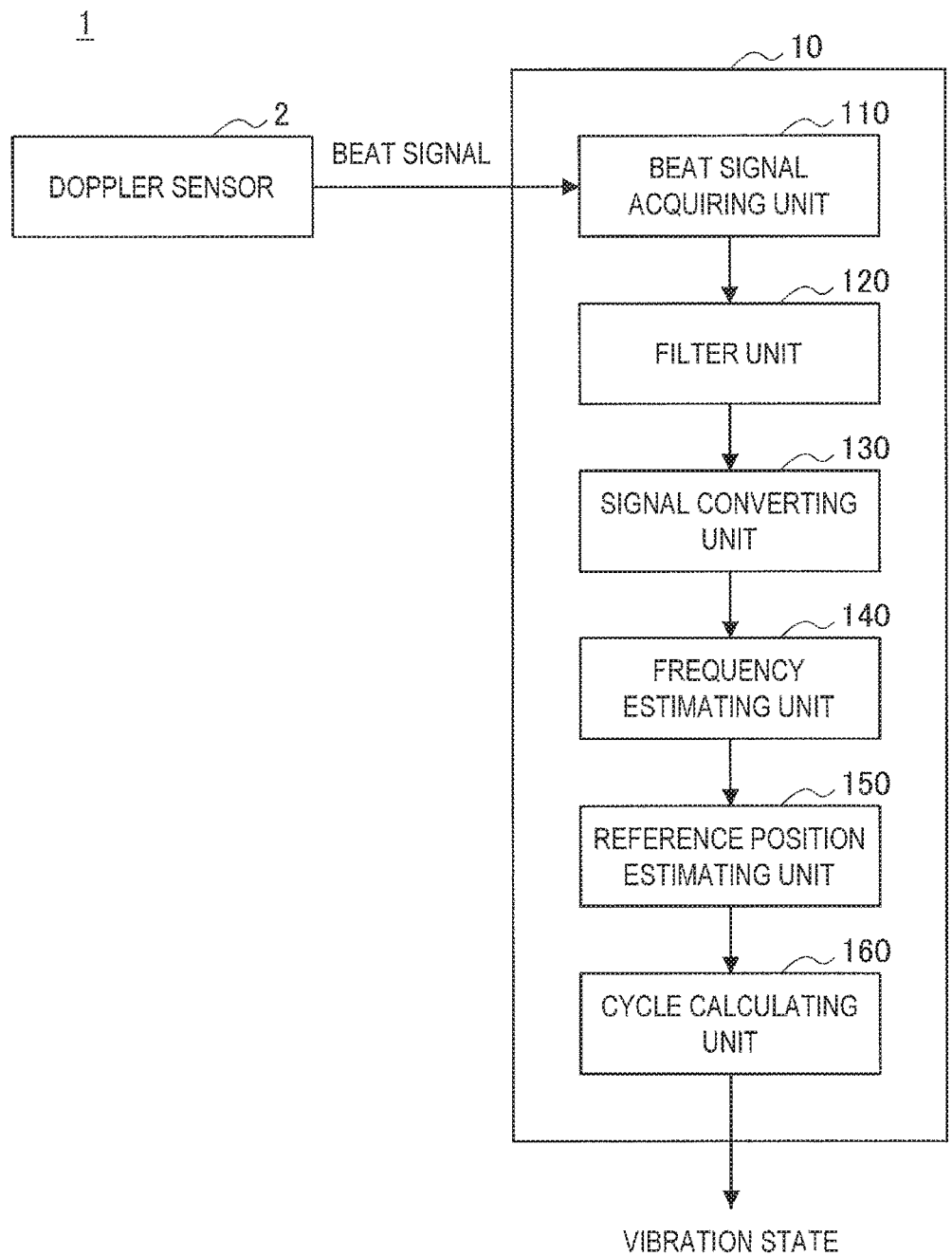
FIG. 2 is a block diagram illustrating an exemplary configuration of a vibration state estimation device according to an embodiment of the present invention.

FIG. 2 is a block diagram illustrating an exemplary configuration of the vibration state estimation device 10 according to an embodiment of the present invention. Referring to FIG. 2, the vibration state estimation device 10 includes a beat signal acquiring unit 110, a filter unit 120, a signal converting unit 130, a frequency estimating unit 140, a reference position estimating unit 150, and a cycle calculating unit 160. The vibration state estimation device 10 illustrated in the drawing converts an acquired beat signal to a one-dimensional signal, and estimates a frequency of the converted one-dimensional signal, and estimates a reference position in the one-dimensional signal for calculating the cycle of the beat signal on the basis of the estimated frequency. Thereby, the vibration of the respiration including fine fluctuation is extracted, and in addition the cycle of the vibration of the respiration including the fine fluctuation is estimated for each cycle of respiration. Thereby, the stress state of the subject can be sensed from variation of the estimated cycle of vibration, for example. In the following, the function of each configuration will be described.

(Beat Signal Acquiring Unit)

The beat signal acquiring unit 110 acquires a beat signal D(t) output from the Doppler sensor 2. The beat signal D(t) output from the Doppler sensor 2 includes two wave components of an I component and a Q component. The beat signal D(t) is expressed by below formula 1, where
the amplitude is A(t),
the wavelength is λ,
the distance between the Doppler sensor 2 and a target object (for example, the person P illustrated in FIG. 1) at time point t is D(t),
the initial phase is $\phi_0$,
the direct current component is O, and
the noise component is w.

$$D(t) = A(t)\exp\left[-j\left(\frac{4\pi}{\lambda}d(t)+\phi_0\right)\right]+O+w \quad \text{Formula 1}$$

The beat signal acquiring unit 110 outputs the acquired beat signal D(t) to the filter unit 120. Although its detail will be described later, when the vibration state estimation device does not include the filter unit 120 in another embodiment, the beat signal acquiring unit 110 may output the beat signal D(t) to the signal converting unit 130. Also, the beat signal acquiring unit 110 may store the acquired beat signal D(t) in the storage unit (not depicted) in temporal sequence.

(Filter Unit)

The filter unit 120 performs a filter process to decrease or remove a low-frequency component such as a direct current component O included in the beat signal D(t) acquired by the beat signal acquiring unit 110, a noise component w, or the like, and outputs the filtered beat signal D(t) to the signal converting unit 130. Thereby, for example, when the amplitude of the beat signal D(t) is small, the beat signal D(t) is amplified by an amplifier (not depicted) or the like. The filter unit 120 may be various filters, such as a low-pass filter, a high-pass filter, a bandpass filter, and an IIR filter, or may be combinations of these filters, for example. Also, the filter unit 120 may reduce components including vibration having no relationship with the respiration, such as body motion and heartbeat of the person P, for example. Although in the present embodiment the filter unit 120 reduces the direct current component O, the noise component w, or the like included in the beat signal D(t), the vibration state estimation device 10 is needless to include the filter unit 120 necessarily, when the filter process for the beat signal D(t) is determined to be unnecessary in another embodiment.

(Signal Converting Unit)

The signal converting unit 130 converts, to a one-dimensional signal r(t), the beat signal D(t) output from the beat signal acquiring unit 110 or the filter unit 120. More specifically, the signal converting unit 130 outputs a one-dimensional signal r(t) that is decided using at least any one of one-dimensional candidate signals converted from the beat signal D(t) by at least two conversion means. The process for estimating the cycle of the vibration of the respiration is made easy by converting the beat signal D(t), which is a two-dimensional signal having an I component a Q component, to the one-dimensional signal r(t). Note that the configuration and the process of the signal converting unit 130 will be described later.

(Frequency Estimating Unit)

The frequency estimating unit 140 estimates the frequency $f_E(t)$ of the one-dimensional signal r(t) output from the signal converting unit 130. For example, the frequency estimating unit 140 may include a first frequency estimating unit that estimates the frequency of the one-dimensional signal r(t) on the basis of the phase difference between the one-dimensional signal r(t) and a reference signal and the temporal change of the phase difference, in order to adjust to fluctuation of a large respiration cycle. Also, the frequency estimating unit 140 may include a second frequency estimating unit that cuts out, from the one-dimensional signal r(t), a comparison signal having a sectional length corresponding to the cycle corresponding to the estimated frequency estimated by the first frequency estimating unit, and estimates the frequency of the one-dimensional signal r(t) by calculating a correlation coefficient between the comparison signal and the one-dimensional signal r(t) having the above sectional length. In the following, the frequency of the one-dimensional signal r(t) estimated by the first frequency estimating unit is referred to as a first estimated frequency $f_A(t)$, and the frequency of the one-dimensional signal r(t) estimated by the second frequency estimating unit is referred to as a second estimated frequency $f_B(t)$.

—First Frequency Estimating Unit

The first frequency estimating unit calculates a first estimated frequency $f_A(t_k)$ from the phase difference $\varphi(t_k)$ between the one-dimensional signal $r(t_k)$ and the reference signal at the time point $t_k$. First, the first frequency estimating unit calculates the phase difference $\varphi(t_k)$ between the one-dimensional signal $r(t_k)$ and the reference signal, by multiplying the one-dimensional signal $r(t_k)$ and the reference signal and extracting the low-frequency component of the multiplied signal by means of the low-pass filter or the like. Here, a sine wave or a cosine wave having parameters of a phase and a temporal change is used as the reference signal, to facilitate the cycle estimation based on the phase change. In that case, the reference signal is the signal of the sine wave or the cosine wave having the first frequency $f_A(t_{k-1})$ estimated at the time point $t_{k-1}$. Then, the first frequency estimating unit calculates the change between the phase difference $\varphi(t_k)$ and the phase difference $\varphi(t_{k-1})$ calculated at the time point $t_{k-1}$. Assuming that the temporal change of the phase difference $\varphi(t_k)-\varphi(t_{k-1})$ is generated by the change of the frequency of the one-dimensional signal r(t), the first frequency estimating unit adds the frequency that corresponds to the temporal change of the phase difference $\varphi(t_k)-\varphi(t_{k-1})$ to the frequency $f_A(t_{k-1})$ of the reference signal, and outputs the first estimated frequency $f_A(t_k)$.

Note that, when the above temporal change of the phase difference is equal to or larger than a predetermined threshold value, the feedback value of the frequency tends to be estimated at a large value, and therefore there is a problem that the first estimated frequency $f_A(t_k)$ vibrates and does not converge. Hence, the value of the frequency that is added to the frequency $f_A(t_{k-1})$ of the reference signal may be a value obtained by multiplying the frequency that corresponds to the temporal change of the phase difference $\varphi(t_k)-\varphi(t_{k-1})$ by a coefficient that is smaller than one. Thereby, the first estimated frequency $f_A(t_k)$ converges in a relatively short time.

Also, when the calculated first estimated frequency $f_A(t_k)$ does not exist in a predetermined frequency band, the frequency $f_A(t_{k-1})$ of the reference signal may be output as the first estimated frequency $f_A(t_k)$. Here, in the present embodiment, a predetermined frequency band means a frequency band that corresponds to the cycle of the respiration motion, for example.

—Second Frequency Estimating Unit

The second frequency estimating unit performs a correlation analysis of the input one-dimensional signal r(t), in order to estimate the second estimated frequency $f_B(t_k)$ whose local change is more accurate than the first estimated frequency $f_A(t_k)$ obtained by the first frequency estimating unit. First, the second frequency estimating unit cuts out a section from the time point $t_k-T_A$ to the time point $t_k$, from the one-dimensional signal r(t), and handles this as the comparison signal. $T_A$ is a cycle corresponding to the first estimated frequency $f_A(t_{k-1})$ estimated previously. Thereafter, the second frequency estimating unit calculates the correlation coefficient on the basis of the comparison signal that is cut out. It is preferable that the calculation range of the correlation coefficient include a range from $t_k-2T_A$ to $t_k-T_A$. Then, the second frequency estimating unit calculates a time lag $\tau_{max}$ at which the correlation coefficient $R(\tau)$ between the one-dimensional signal r(t) having the sectional length $T_A$ and the comparison signal is at the maximum, in the above calculation range. In this case, the second frequency estimating unit may store the correlation coefficient $R(\tau_{max})$ at the time of $\tau=\tau_{max}$, in a storage unit (not depicted). The second frequency estimating unit calculates the second estimated frequency $f_B(t_k)$ from the time lag $\tau_{max}$ when the correlation coefficient calculated in the correlation coefficient calculation range is at the maximum. For example, the second estimated frequency $f_B(t_k)$ may be a reciprocal of the time lag $\tau_{max}$.

—Determination Unit

The frequency estimating unit 140 may include a determination unit that determines which frequency to use with respect to the above two estimated frequencies. For example, the determination unit may determine which frequency is to be used as the estimated frequency $f_E(t)$ on the basis of whether the difference between the two estimated frequencies is equal to or smaller than a predetermined threshold value. Also, the determination unit may determine which one of the first estimated frequency $f_A(t_k)$ and the second estimated frequency $f_B(t_k)$ is to be used, on the basis of the value of the time lag $\tau_{max}$ calculated at the second frequency estimating unit.

From the above, the frequency estimating unit 140 estimates the frequency of the waveform including much fine fluctuation highly accurately for each cycle of respiration, by determining, by the determination unit, which one of the first frequency estimating unit that roughly estimates a frequency and the second frequency estimating unit that has difficulty in following irregular fluctuation but estimates a frequency by detecting the local change of the waveform is to be used. The estimated frequency $f_E(t)$ estimated by the frequency estimating unit 140 is output to the reference position estimating unit 150.

(Reference Position Estimating Unit)

The reference position estimating unit 150 estimates the reference position of the one-dimensional signal r(t) on the basis of the estimated frequency $f_E(t)$. Here, in the present specification, the reference position means a position having a common feature, such as a peak position, in similar waveforms of one cycle in the one-dimensional signal r(t). The one-dimensional signal r(t) is a time-series signal, and thus the reference position is specified by a time point. Also, the reference position may be a bottom position of the waveform, or may be a position where r(t)=0, for example.

First, the reference position estimating unit 150 cuts out a reference signal having a sectional length of the cycle $T_E$ corresponding to the estimated frequency $f_E(t_k)$ and having the estimated time point $t_k$ at the end point, from the one-dimensional signal r(t). The reference position estimating unit 150 estimates the reference position of the cut reference signal. For example, the reference position estimating unit 150 may generate a cosine wave or a sine wave of a predetermined initial phase (in the present embodiment, the initial phase is 0) having the same cycle $T_E$ as the reference signal, and calculate the phase difference between the above cosine wave or sine wave and the reference signal. Here, the reference position in the reference signal section of the one-dimensional signal r(t) can be estimated from the calculated phase difference and the time point $t_k$.

Note that, in order to correct an error of the estimated reference position, the reference position estimating unit 150 may decide the reference position, using a statistical means, from the distribution of reference positions estimated a plurality of times in the above reference signal section. For example, the reference position estimating unit 150 may decide a mode (a mode value) obtained from the distribution of reference positions, as the reference position.

From the above, the reference position estimating unit 150 estimates the reference position of the one-dimensional signal r(t), in order to derive information for calculating the cycle even from the waveform including the fine fluctuation. The reference position estimating unit 150 outputs the estimated or decided reference position to the cycle calculating unit 160.

(Cycle Calculating Unit)

The cycle calculating unit 160 calculates the cycle of the beat signal D(t), from a plurality of reference positions output from the reference position estimating unit 150. Specifically, the cycle calculating unit 160 may calculate the difference between the reference positions next to each other, as one cycle of the beat signal D(t). Thereby, the cycle of the respiration vibration expressed by the waveform including fine fluctuation can be calculated for each cycle of respiration.

<3. Exemplary Configuration of Signal Converting Unit>

Figure 3:
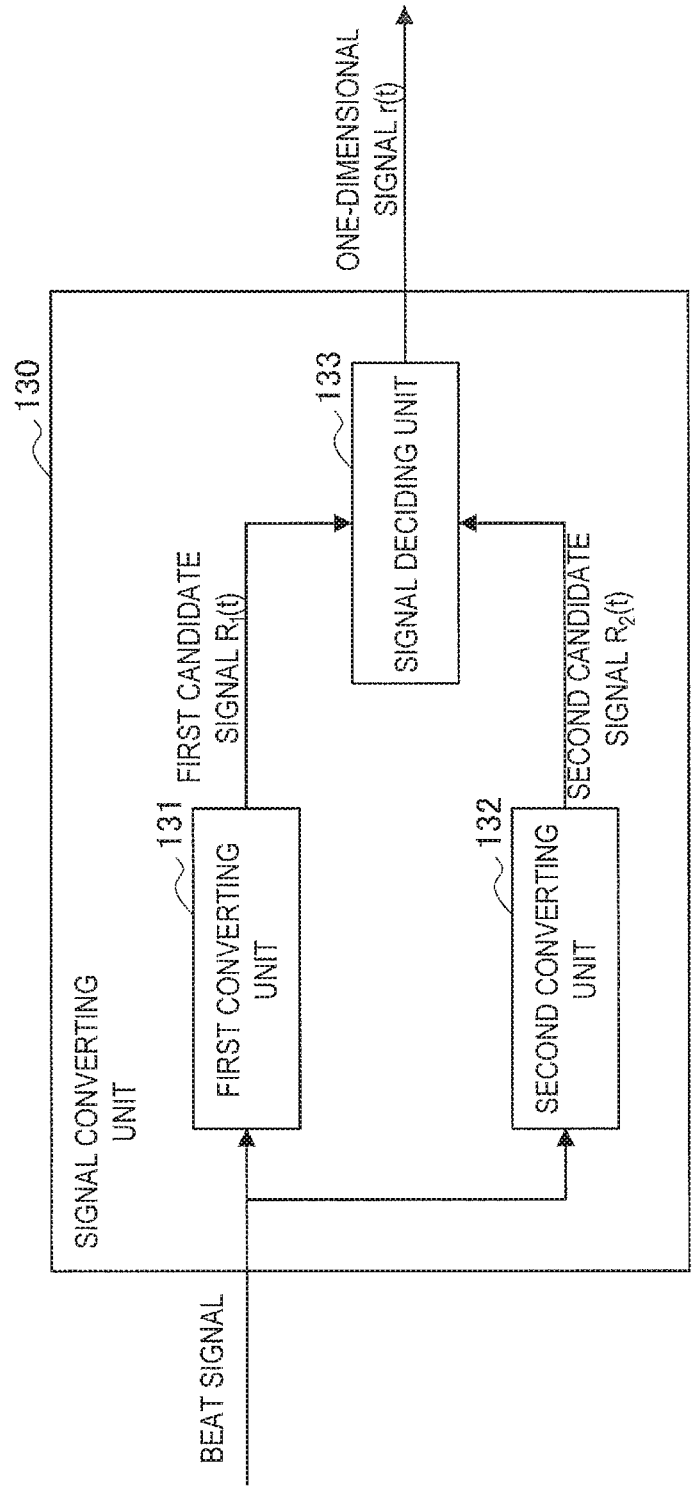
FIG. 3 is a block diagram illustrating an exemplary configuration of a signal converting unit according to an embodiment of the present invention.

FIG. 3 is a block diagram illustrating the exemplary configuration of the signal converting unit 130 according to an embodiment of the present invention. Referring to FIG. 3, the signal converting unit 130 includes a first converting unit 131, a second converting unit 132, and a signal deciding unit 133. In the following, each component will be described.

(First Converting Unit)

The first converting unit 131 converts the beat signal D(t) to a one-dimensional first candidate signal $R_1(t)$ on the basis of the distribution on the IQ plane of the beat signal D(t), and outputs the converted first candidate signal $R_1(t)$ to the signal deciding unit 133, with respect to the beat signal D(t) acquired from the beat signal acquiring unit 110 or the filter unit 120. For example, the first converting unit 131 may calculate an inner product of the two-dimensional vector expressing the beat signal D(t) and the eigenvector corresponding to the maximum eigenvalue of the covariance matrix of the beat signal D(t), in order to convert the beat signal D(t) to the first candidate signal $R_1(t)$. That is, the first converting unit 131 can obtain the first candidate signal $R_1(t)$ obtained by projecting the beat signal D(t) in the principal component direction corresponding to the maximum eigenvalue. Specifically, the first candidate signal $R_1(t)$ may be calculated by below formula 2.

$$R_1(t) = p(t)b(t) \qquad \text{Formula 2}$$

Here, b(t) is a two-dimensional vector expressing I component and Q component of the beat signal D(t), and p(t) is an eigenvector corresponding to the maximum eigenvalue of the covariance matrix of the beat signal D(t). Note that the origin of the two-dimensional vector expressing the beat signal D(t) may be estimated on the basis of the distribution of the beat signal D(t), for example. For example, the midpoint of the maximum position and the minimum position from the origin of the IQ plane, of the trajectory of the beat signal D(t) in the past several seconds to several ten seconds may be the origin. Also, when the trajectory of the beat signal D(t) is approximated as a circle or an ellipse by a least squares method or the like, the center point of the approximated pictorial figure may be the origin. Also, the beat signal filtered by a high-pass filter or a bandpass filter in the filter unit 120 is adjacent to the origin of the IQ plane, and therefore the origin of the IQ plane may be the origin of the two-dimensional vector.

Figure 4:
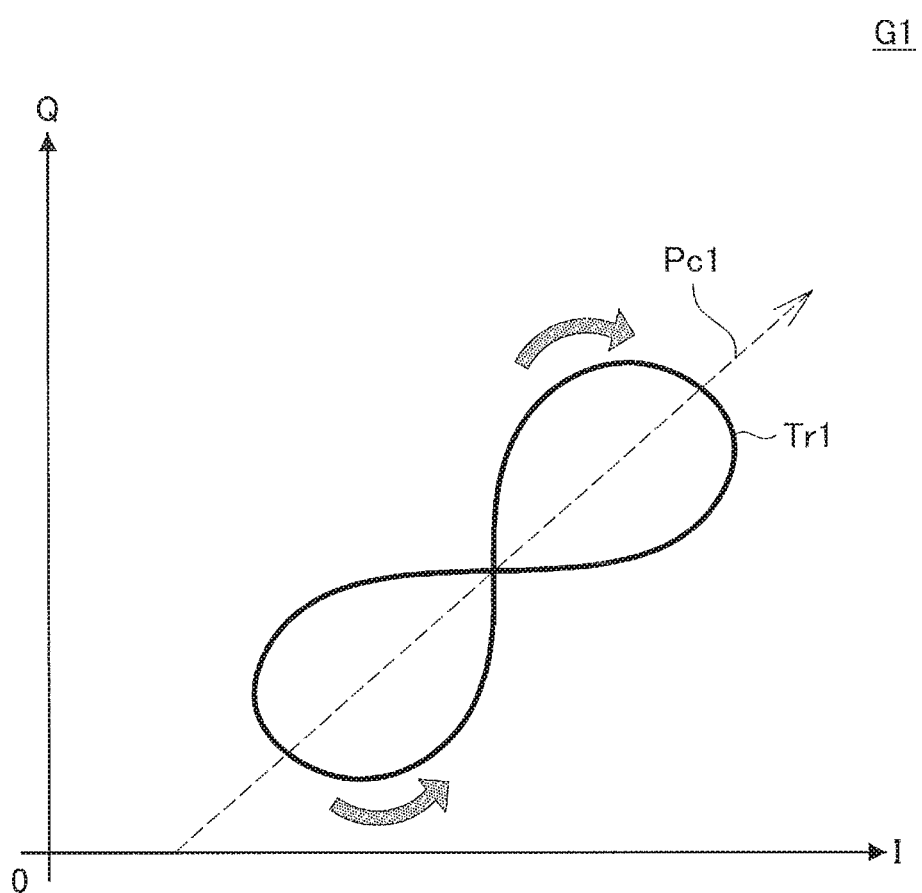
FIG. 4 is a diagram illustrating an example of a trajectory in an IQ plane of a beat signal.

FIG. 4 is a diagram illustrating an example of the trajectory on the IQ plane of the beat signal D(t). Referring to the graph G1 illustrated in FIG. 4, a trajectory Tr1 of the beat signal D(t) is illustrated on the IQ plane. For example, when the displacement of the vibration of the respiration is comparatively small, for example approximately 1/10 of the wavelength of the radiation wave radiated from the Doppler sensor 2, the beat signal D(t) is a flattened figure-of-8 distribution, such as the trajectory Tr1, in many cases. In this case, when principal component analysis is performed with respect to the trajectory Tr1 for example, the maximum eigenvalue for the first principal component indicated by the axis Pc1 indicates a larger value as compared with other principal components. The first converting unit 131 can obtain the first candidate signal $R_1(t)$ by projecting the beat signal D(t) on the first principal component.

Note that the first converting unit 131 according to the present embodiment converts the beat signal D(t) to the first candidate signal $R_1(t)$, using the eigenvalue and the eigenvector obtained by performing the principal component analysis or the like with respect to the trajectory Tr1. However, for example, if it is possible to extract the axis direction of the flattened direction and to extract the motion of the signal in the axis direction with respect to the flattened figure-of-8 distribution such as the trajectory Tr1, the first converting unit 131 may convert the beat signal D(t) to the first candidate signal $R_1(t)$ using the method other than the principal component analysis.

(BACKGROUND)

Figure 5:
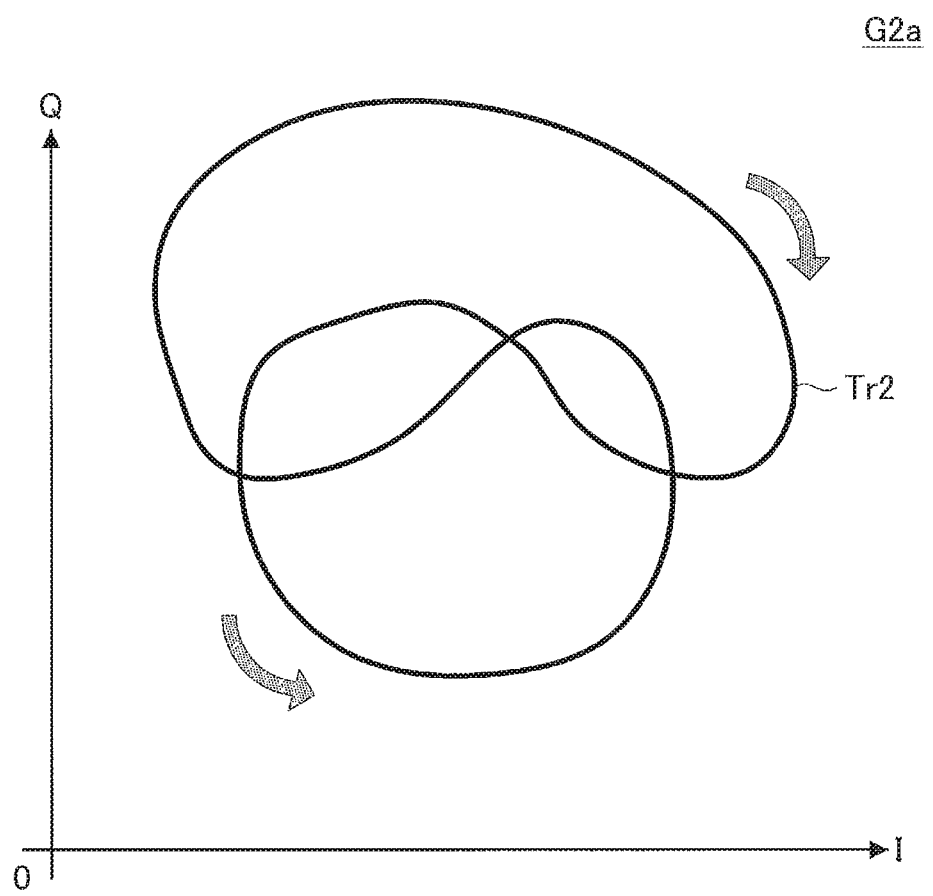
FIG. 5 is a diagram illustrating an example of a trajectory in an IQ plane of a beat signal.

However, when the displacement of the vibration of the respiration is comparatively large, the waveform of the first candidate signal $R_1(t)$ converted from the beat signal D(t) by the above first converting unit 131 does not necessarily express the vibration of the respiration accurately. FIG. 5 is a diagram illustrating an example of the trajectory in the IQ plane of the beat signal D(t). Referring to the graph G2a illustrated in FIG. 5, a trajectory Tr2 of the beat signal D(t) on the IQ plane is illustrated. For example, when the displacement of the vibration of the respiration is comparatively large, for example equal to or larger than 1/2 of the wavelength of the radiation wave radiated from the Doppler sensor 2, the distribution depicts a circular arc, like the trajectory Tr2, in many cases. When principal component analysis is performed for the distribution of the beat signal D(t) expressed by this trajectory Tr2, the value of the maximum eigenvalue becomes low, and thus it is difficult to set the principal component direction appropriately. Also, even when the axis indicating the principal component direction is obtained appropriately, the first candidate signal $R_1(t)$ obtained by the first converting unit 131 can have a shape including the high-frequency signal having a shorter cycle than the real respiration cycle.

Figure 6:
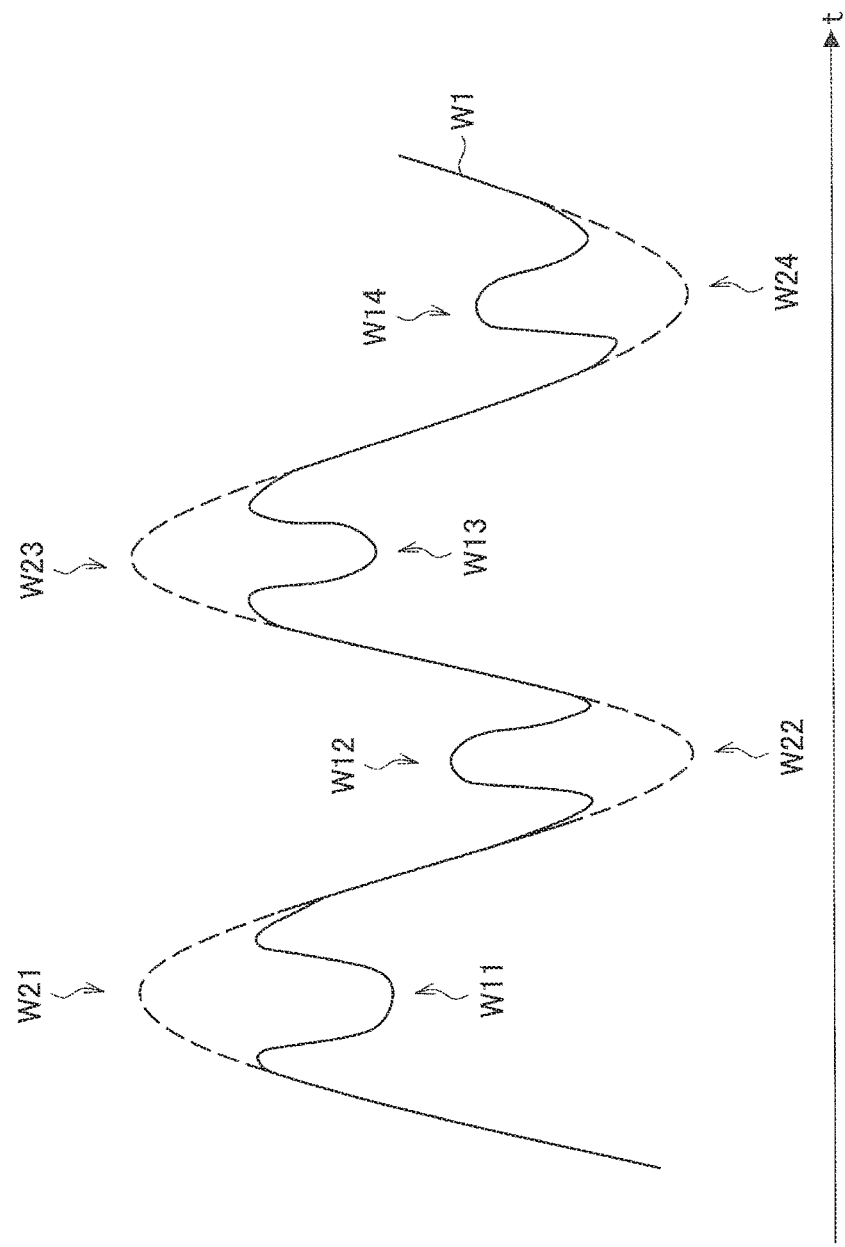
FIG. 6 is a diagram illustrating an example of a first candidate signal output by a first converting unit according to an embodiment of the present invention.

FIG. 6 is a diagram illustrating an example of the first candidate signal $R_1(t)$ output by the first converting unit 131 according to an embodiment of the present invention. Referring to FIG. 6, a wave W1 indicating a temporal change of the first candidate signal $R_1(t)$ is illustrated. In this case, the wave W1 includes distortions W11 to W14 by a high-frequency component. This is because either the moving direction of the beat signal D(t) reverses by switching or fluctuation of the respiration, or the beat signal D(t) moves to draw a circular arc a plurality of times during one cycle of respiration, so that the wave W1 of the first candidate signal $R_1(t)$ projected in the principal component direction includes the vibration of a shorter cycle (high-frequency wave) than the cycle of the respiration. Hence, when the displacement of the vibration of the respiration is equal to or larger than ½ of the wavelength of the radiation wave of the Doppler sensor 2 for example, the waveform of the first candidate signal $R_1(t)$ converted by the first converting unit 131 includes distortions by the high-frequency component, unlike the waveform that represents the vibration of the actual respiration (in the example illustrated in FIG. 6, the waveform of the wave W1 including waveforms W21 to W24). As a result, for example, when the waveform of the one-dimensional signal r(t) includes a high-frequency signal, it can be difficult to determine the cycle of the vibration on the basis of the waveform.

Thus, the signal converting unit 130 further includes the second converting unit 132 that converts the beat signal D(t) to a one-dimensional second candidate signal $R_2(t)$, reflecting the temporal change of the position of the beat signal D(t). The second converting unit 132 can extract the vibration of respiration of a large displacement that is difficult to extract accurately in the first converting unit 131. Specifically, the second converting unit 132 is capable of obtaining the one-dimensional signal by tracking the sequential change of the beat signal D(t), instead of the distribution of the beat signal D(t).

(Second Converting Unit)

The second converting unit 132 converts the beat signal D(t) to a one-dimensional second candidate signal $R_2(t)$ on the basis of the temporal change of the position on the IQ plane of the beat signal D(t), and outputs the converted second candidate signal $R_2(t)$ to the signal deciding unit 133, with respect to the beat signal D(t) acquired from the beat signal acquiring unit 110 or the filter unit 120. For example, the second converting unit 132 may convert the beat signal D(t) to the second candidate signal $R_2(t)$, by calculating the product of the distance (corresponding to amplitude) to the position of the beat signal D(t) from the center of the distribution estimated on the basis of the distribution on the IQ plane of the beat signal D(t) and the amount of change of the rotation angle of the beat signal D(t) with respect to the center of the distribution. For example, $R_2(t)$ may be calculated by a function utilizing a continuous function (in the present embodiment, a sigmoid function) in below formula 3.

$$R_2(t)=a[1+\exp(b \cdot Amp(t)\theta'(t)-c)]^{-1} \quad \text{Formula 3}$$

Here,

Amp(t) is the amplitude of the beat signal D(t),

θ(t) is the angle on the IQ plane of the beat signal D(t), and

θ'(t) is the angle change amount of the angle θ(t) per unit time or the time derivative value of the angle θ(t). Also, each of a, b, and c is a constant and is freely settable.

Figure 7:
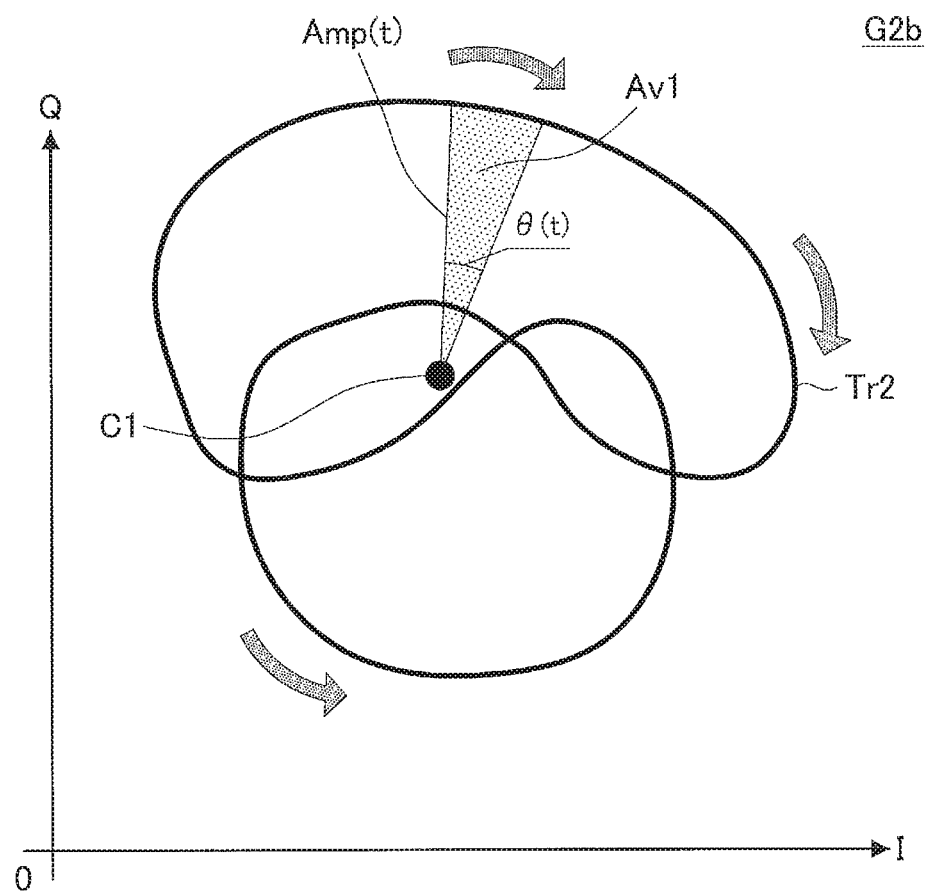
FIG. 7 is a diagram illustrating an example in which a conversion process is performed by a second converting unit according to an embodiment of the present invention with respect to a trajectory in an IQ plane of a beat signal.

FIG. 7 is a diagram illustrating an example in which a conversion process is performed by the second converting unit 132 with respect to the trajectory on the IQ plane of the beat signal D(t). Referring to the graph G2b illustrated in FIG. 7, the amplitude Amp(t) and the angle θ(t) are illustrated with respect to the beat signal D(t) on the trajectory Tr2. The product of the amplitude Amp(t) and the amount of change θ'(t) of the angle θ(t) corresponds to the areal velocity of the region Av1 illustrated in FIG. 7. This areal velocity corresponds to the amplitude of the vibration of the respiration per unit time. Also, the amount of change θ'(t) is a positive or negative value, depending on the direction of the vibration of the respiration (inhale and exhale of breath), and thus can express the direction of the vibration of the respiration. Hence, the state of the respiration motion is expressed adequately by the product of the amplitude Amp(t) and the amount of change θ'(t).

Note that the amplitude Amp(t) corresponds to the distance to the position of the beat signal D(t) from the center of the distribution estimated on the basis of the distribution on the IQ plane of the beat signal D(t), and the angle θ(t) corresponds to the rotation angle of the beat signal D(t) with respect to the center of the distribution. Here, the center of the distribution indicates the center point C1 illustrated in FIG. 7, for example. Here, the center of the distribution of the beat signal D(t) may be estimated on the basis of the distribution of the beat signal D(t). For example, the intermediate position between the maximum position and the minimum position from the origin of the IQ plane, or the position that corresponds to the center of the distribution may be the center of the distribution of the beat signal D(t), with respect to the distribution of the beat signal D(t) in the past several seconds to several ten seconds. Also, when the trajectory of the beat signal D(t) is approximated as a circle or an ellipse by a least squares method or the like, the center point of the approximated pictorial figure may be the center of the distribution. Also, the beat signal D(t) filtered by a high-pass filter or a bandpass filter in the filter unit 120 is distributed adjacent to the origin of the IQ plane, and thus the origin of the IQ plane may be the center of the distribution of the beat signal D(t).

(Signal Deciding Unit)

The signal deciding unit 133 decides the one-dimensional signal r(t) output to the frequency estimating unit 140, by selecting at least one of the first candidate signal $R_1(t)$ and the second candidate signal $R_2(t)$ on the basis of the first candidate signal $R_1(t)$ output from the first converting unit 131 and the second candidate signal $R_2(t)$ output from the second converting unit 132. For example, the signal deciding unit 133 may decide one of the first candidate signal $R_1(t)$ and the second candidate signal $R_2(t)$ as the one-dimensional signal r(t). Also, the signal deciding unit 133 may decide a signal in which the first candidate signal $R_1(t)$ and the second candidate signal $R_2(t)$ are merged as the one-dimensional signal r(t).

With regard to the trajectory Tr1 of the beat signal D(t) illustrated in FIG. 4 in the case of small vibration of the respiration, the amount of change θ'(t) of the angle θ(t) from the center of the distribution becomes less accurate due to the influence of noise and quantization error, as compared with the trajectory Tr2 of the beat signal D(t) illustrated in FIG. 5. That is, when the vibration of the respiration is small, the first candidate signal $R_1(t)$ can express the waveform of the vibration of the respiration more accurately than the second candidate signal $R_2(t)$. On the other hand, as described above, with regard to the trajectory Tr2 of the beat signal D(t) illustrated in FIG. 5 in the case of large vibration of the respiration, the second candidate signal $R_2(t)$ can express the waveform of the vibration of the respiration more accurately than the first candidate signal $R_1(t)$. Hence, the signal deciding unit 133 compares respectively with respect to the first candidate signal $R_1(t)$ or the second candidate signal $R_2(t)$, and decides the output one-dimensional signal r(t) on the basis of the comparison result.

Here, the signal deciding unit 133 decides an evaluation value s, as a parameter for deciding the one-dimensional signal r(t). The evaluation value s is a value for evaluating which one of the second candidate signal $R_2(t)$ and the first candidate signal $R_1(t)$, in which the accuracy of the waveform that expresses the vibration of the respiration changes in response to the displacement of the vibration of the respiration, is to be used preferentially. That is, the waveform reflecting the vibration of the respiration more accurately can be generated, by calculating the evaluation value s and deciding the one-dimensional signal r(t) on the basis of the evaluation value s, regardless of the displacement of the vibration of the respiration. The evaluation value s may be a value that is decided between 0 and 1, for example. In this case, for example, when the evaluation value s is close to 0, the first candidate signal $R_1(t)$ expresses the waveform of the vibration of the respiration more accurately than the other candidate signal, and when the evaluation value s is close to 1, the second candidate signal $R_2(t)$ expresses the waveform of the vibration of the respiration more accurately than the other candidate signal. Also, although in the present embodiment the evaluation value s is a single value, the evaluation value s is not limited to such an example in other embodiments. For example, the evaluation value s may be calculated for each of the first candidate signal $R_1(t)$ and the second candidate signal $R_2(t)$, and the signal deciding unit 133 may decide the one-dimensional signal r(t) to output, on the basis of the evaluation value s of each candidate signal. Also, the numerical value range of the evaluation value s is not limited to the range of 0 to 1, but may be any range.

In the following, a one-dimensional signal r(t) deciding process flow in the signal deciding unit 133, as well as a method for deciding the evaluation value s, will be described.

<4. Signal Deciding Process Flow>

Figure 8:
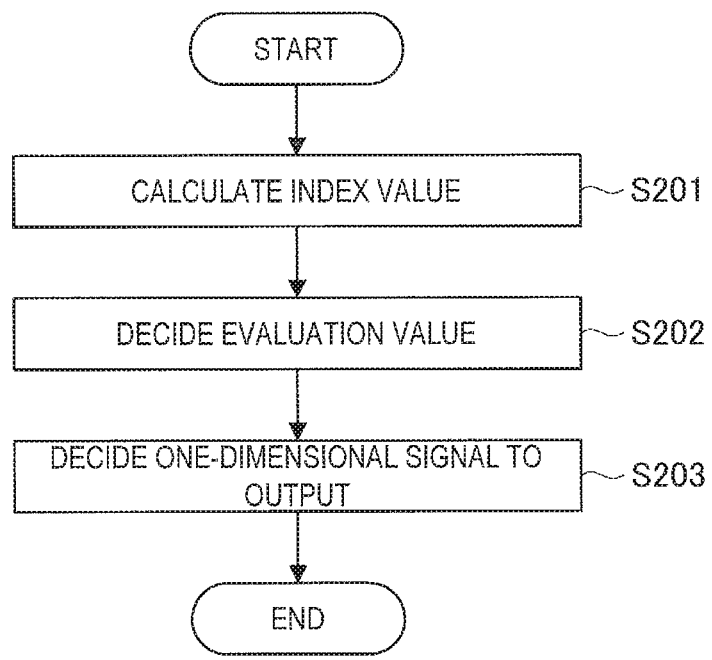
FIG. 8 is a diagram illustrating an example of a one-dimensional signal deciding process flow in a signal deciding unit according to an embodiment of the present invention.

FIG. 8 is a diagram illustrating an example of the one-dimensional signal r(t) deciding process flow in the signal deciding unit 133 according to an embodiment of the present invention. First, the signal deciding unit 133 according to the present embodiment calculates an index value for deciding the evaluation value s, and thereafter the signal deciding unit 133 decides the evaluation value s, using the calculated index value. Thereafter, the signal deciding unit 133 decides the one-dimensional signal r(t), using the decided evaluation value s.

[4-1. Calculation of Index Value]

First, the signal deciding unit 133 executes a process to calculate an index value for deciding the evaluation value s for selecting at least one of the first candidate signal $R_1(t)$ and the second candidate signal $R_2(t)$ (S201). The signal deciding unit 133 calculates, using at least one of below two means, for example.

(Calculation of Index Value by Frequency)

Signal deciding unit 133 is capable of selecting at least one of the candidate signals, on the basis of the evaluation value s decided by comparing the feature value of the first candidate signal $R_1(t)$ and the feature value of the second candidate signal $R_2(t)$, for example. In the present embodiment, this feature value may be the frequency of each candidate signal, for example. That is, the signal deciding unit 133 may calculate the frequency of each of the first candidate signal $R_1(t)$ and the second candidate signal $R_2(t)$, and decide the evaluation value s by comparing both of the frequencies. As described above, when the displacement of the vibration of the respiration is comparatively large, for example equal to or larger than ½ of the wavelength of the radiation wave radiated from the Doppler sensor 2, the first candidate signal $R_1(t)$ can form a waveform including a high-frequency component, as illustrated in FIG. 6. In that case, the frequency of the first candidate signal $R_1(t)$ can be a high value, as compared with the frequency of the second candidate signal $R_2(t)$. On the other hand, when the first candidate signal $R_1(t)$ does not include much high-frequency component, each frequency can be approximately the same value. Thus, the signal deciding unit 133 is capable of deciding the evaluation value s for selecting one or both of the first candidate signal $R_1(t)$ and the second candidate signal $R_2(t)$, by comparing the frequencies of both candidate signals.

Here, the signal deciding unit 133 may calculate the index value $x_1(t)$ for deciding the evaluation value s, on the basis of the frequency of each candidate signal. For example, the signal deciding unit 133 may calculate the index value $x_1(t)$ for deciding the evaluation value s, using below formula 4, assuming that the frequency of the first candidate signal $R_1(t)$ is $f_{r1}(t)$, and that the frequency of the second candidate signal $R_2(t)$ is $f_{r2}(t)$.

$$x_1(t)=(f_{r1}(t)+k)/(f_{r2}(t)+k) \quad \text{Formula 4}$$

Here, k is a constant, and a value of approximately 0.0 to 1.0 is preferable. For example, when k equals to 1, and the displacement of the vibration of the respiration is comparatively large, the index value $x_1(t)$ is a value larger than 1.0 if the high-frequency component is included in the first candidate signal $R_1(t)$. On the other hand, when the first candidate signal $R_1(t)$ does not include much high-frequency component, the index value $x_1(t)$ is a value close to approximately 1.0.

Note that the frequency of each candidate signal may be calculated from the change of the phase of an analysis signal having a complex component obtained by using Hilbert transformation with respect to each candidate signal, for example. In general, Hilbert transformation can convert an input signal to an analysis signal having a complex component including the input signal as a real part and a signal after passing through a π/2 phase delay device as an imaginary part. Thereby, for example, the frequency of the candidate signal that is the input signal can be calculated by extracting the temporal change of the phase of the analysis signal at sequential two time points. Although in the present embodiment the frequency of each candidate signal is calculated by the analysis signal obtained by Hilbert transformation, the above frequency calculation method is not limited to such an example. For example, the peak frequency component of each candidate signal can be calculated using discrete fourier transform (DFT), wavelet analysis, or the like. Note that, as described above, each candidate signal includes a one-dimensional waveform including fine fluctuation, and therefore, if each candidate signal is converted to a frequency region by fourier transform or the like, it is concerned that the above information relevant to the frequency component that expresses the fine fluctuation is diluted. Hence, it is preferable to calculate a frequency by a method that analyzes in the time region, such as Hilbert transformation, with respect to each candidate signal.

(Calculation of Index Value by Angle Change Amount)

Also, the signal deciding unit 133 may decide the evaluation value s according to the amount of change of the rotation angle of the beat signal D(t) with respect to the center of the distribution estimated on the basis of the distribution on the IQ plane of the beat signal D(t) before converting. Here, the center of the distribution and the rotation angle mean the center of the distribution and the rotation angle θ(t) in the calculation method of the second candidate signal $R_2(t)$ used in the second converting unit 132. For example, when the displacement of the vibration of the respiration is comparatively small, the change of the amount of change θ'(t) of the rotation angle θ(t) is also comparatively small. On the other hand, when the displacement of the vibration of the respiration is comparatively large, the change of θ'(t) is also comparatively large. Hence, the displacement of the vibration of the respiration can be checked on the basis of the magnitude and the deviation of θ'(t). That is, the evaluation value s for selecting one or both of the first candidate signal $R_1(t)$ and the second candidate signal $R_2(t)$ can be decided by evaluating the change of θ'(t).

For example, the signal deciding unit 133 may calculate an index value $x_2(t)$ for deciding the evaluation value s, on the basis of the deviation of the amount of change θ'(t) of the angle, using below formula 5.

$$x_2(t) = \int_{t-L}^{t} (\theta'(u) - E[\theta'(u)])^2 du \qquad \text{Formula 5}$$

Here, L is an arbitrary delay time, and E is an expected value. For example, when the vibration of the respiration is comparatively small, the value of the index value $x_2(t)$ is small. On the other hand, when the vibration of the respiration is comparatively large, the value of the index value $x_2(t)$ is large.

Note that, when the vibration of the respiration is comparatively small, the rotation angle of the beat signal D(t) is small, and therefore the amount of change θ'(t) indicates an abnormal value in many cases. Hence, for example, the signal deciding unit 133 may correct the value of θ'(t) when the vibration of the respiration is comparatively small, by performing a smoothing process by a median filter or moving average, an outlier removing process, or the like with respect to the distribution of the amount of change θ'(t). Thereby, each candidate signal is selected on the basis of the amount of change θ'(t) more appropriately. Also, the value of the amount of change θ'(t) is small when the vibration of the respiration is small, and is large when the vibration of the respiration is large. Hence, for example, the value of the index value $x_2(t)$ may be calculated by comparing θ'(t) and a predetermined threshold value, or may be calculated on the basis of a Mahalanobis distance decided from the distribution of the amount of change θ'(t).

(Other Index Values)

Although in the present embodiment each of the index values $x_1(t)$ and $x_2(t)$ is calculated on the basis of the frequency of each candidate signal and the amount of change of the angle of the beat signal D(t), the present invention is not limited to such an example, but the index values may be calculated by various methods. For example, the signal deciding unit 133 may calculate the index values on the basis of the feature included in the amplitude of each candidate signal. More specifically, the signal deciding unit 133 may compare the amplitudes at the same time point of the first candidate signal $R_1(t)$ and the second candidate signal $R_2(t)$, and calculate the index values for deciding the evaluation value s on the basis of the distribution of comparison results at a plurality of time points and the comparison result at the above time point. Thereby, the value of the evaluation value s may be decided in such a manner that another candidate signal is used immediately when the amplitude of one of the candidate signals is abnormal. Also, the signal deciding unit 133 may normalize the amplitudes of both candidate signals, when calculating the index values on the basis of the feature included in the amplitudes. Thereby, features other than the magnitudes of the amplitudes of the both candidate signals are extracted easily, and the number of factors for deciding the evaluation value s is increased.

[4-2. Decision of Evaluation Value]

The signal deciding unit 133 executes a process for deciding the evaluation value s, on the basis of at least one of the distributions of the calculated index values $x_1(t)$ and $x_2(t)$ (S202). For example, the signal deciding unit 133 may decide the evaluation value s, by comparing at least one of the calculated index values $x_1(t)$ and $x_2(t)$ with a predetermined threshold value. Also, the signal deciding unit 133 may decide the evaluation value s, using a model optimized by a machine learning method, with respect to at least one of the index values $x_1(t)$ and $x_2(t)$. For example, the signal deciding unit 133 may decide the evaluation value s, using discriminant analysis such as Mahalanobis distance and linear discriminant function, relevance vector machine (RVM), logistic regression such as sparse logistic regression and Bayesian logistic regression, and, neural network including deep learning or the like. In the following, an example of the decision method of the evaluation value s will be described.

(Evaluation Based on Distribution of Index Value)

For example, the signal deciding unit 133 may set the evaluation value s at either one of 0 and 1, on the basis of whether or not at least one of the calculated index values $x_1(t)$ and $x_2(t)$ is equal to or larger than a predetermined threshold value. Also, the signal deciding unit 133 may set the evaluation value s between 0 and 1, on the basis of the difference between at least one of the index values $x_1(t)$ and $x_2(t)$ and the above predetermined threshold value.

Figure 9:
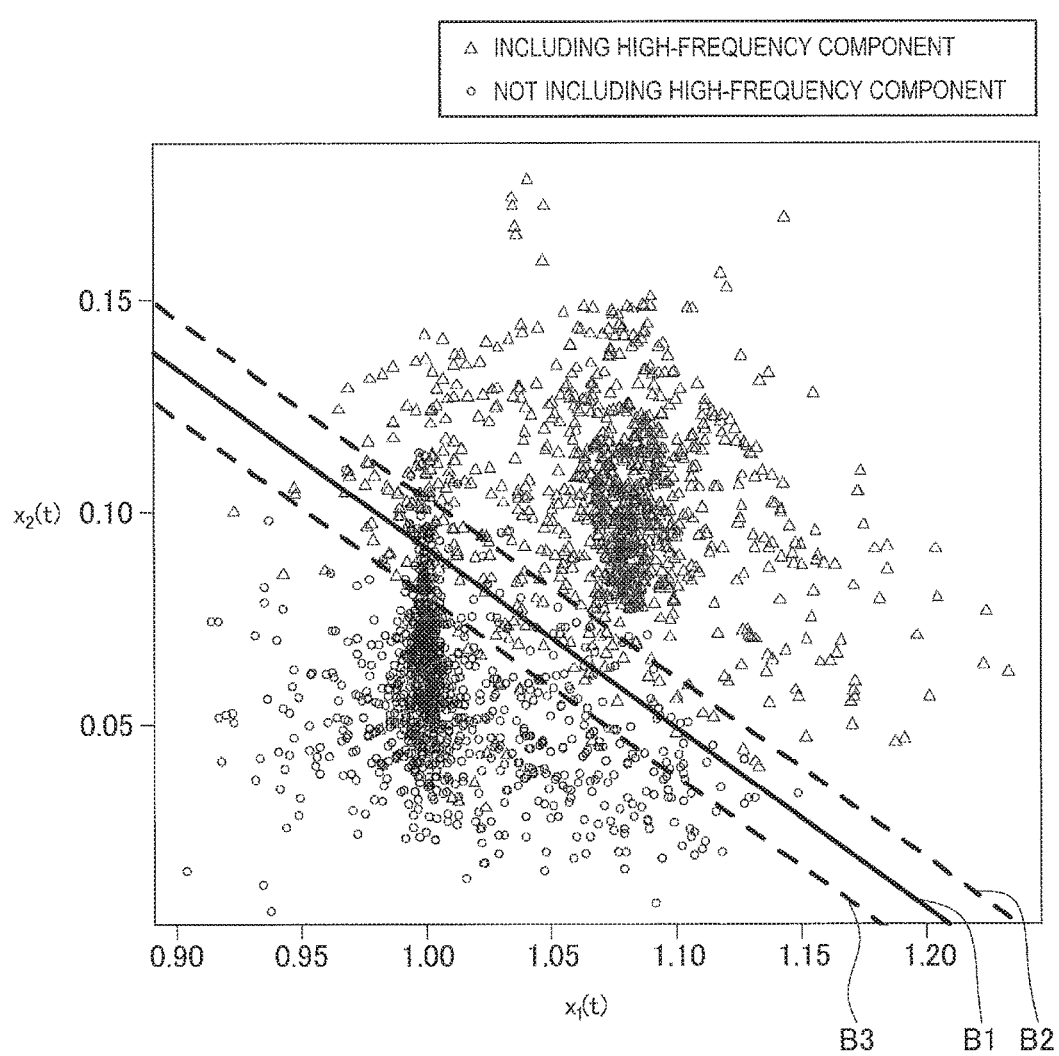
FIG. 9 is a diagram illustrating a distribution of an index value calculated by a signal deciding unit according to an embodiment of the present invention.

FIG. 9 is a diagram illustrating the distribution of the index values calculated by the signal deciding unit 133 according to an embodiment of the present invention. The horizontal axis indicates the index value $x_1(t)$, and the vertical axis indicates the index value $x_2(t)$. Note that the index value $x_1(t)$ is a value calculated by formula 4 (k=1), and the index value $x_2(t)$ is a value calculated by formula 5. Also, in the drawing, a triangle indicates a case in which a high-frequency component is included in the first candidate signal $R_1(t)$, and a circle indicates a case in which a high-frequency component is not included in the first candidate signal $R_1(t)$. Referring to FIG. 9, when both of the index values $x_1(t)$ and $x_2(t)$ indicate comparatively high values (when plotted in the area above the boundary B1), there are many waveforms including high-frequency components. In this case, for example, the evaluation value s may be decided in such a manner that the second candidate signal $R_2(t)$, which is less likely to include a high-frequency component, is selected when the indicated index value is plotted in the area above the determination boundary B1 as a determination boundary. Specifically, the signal deciding unit 133 may set the evaluation value s at 1, when the index value is plotted in the area above the determination boundary B1, and may set the evaluation value s at 0, when the index value is plotted in and the area blow the determination boundary B1. Thereby, the evaluation value s can be decided easily. Also, the signal deciding unit 133 may decide the evaluation value s on the basis of the distance between a point plotted for the index values $x_1(t)$ and $x_2(t)$ and the determination boundary B1.

Also, the signal deciding unit 133 may calculate the evaluation value s, using any function, on the basis of the distance between the plotted point and the determination boundary B1. In this case, the signal deciding unit 133 may calculate the evaluation value s, using a function in which the evaluation value s of the determination boundary B1 is 0.5, and the evaluation value s on the dashed line B2 is 0.75, and the evaluation value s on the dashed line B3 is 0.25, for example. Thereby, the evaluation value s can be decided more appropriately. Also, although in the example illustrated in FIG. 9 the evaluation value s can be calculated on the basis of a simple linear determination boundary B1, a determination boundary may be set on the basis of Bayesian identification rule, support vector machine (SVM), kernel trick, or the like, for example. Thereby, a more appropriate evaluation value s can be decided.

(Evaluation by Logistic Regression)

Also, the signal deciding unit 133 may decide the evaluation value s, on the basis of a statistical identification model built by logistic regression. Here, the evaluation value s is defined by a sigmoid function of formula 6, and the statistical identification model for calculating the evaluation value s is built by the logistic regression given as the likelihood p(y|w) in formula 7. Note that σ(x) means a sigmoid function in formulas 6 and 7.

$$s = \sigma(w^T x_n) \qquad \text{Formula 6}$$

$$p(y \mid w) = \prod_{n=1}^{N} \sigma(w^T x_n)^{y_n} \left[1 - \sigma(w^T x_n)^{1-y_n}\right] \qquad \text{Formula 7}$$

Note that,
Y is a teacher data,
W is a learning parameter,
$X_n$ is a vector in which index values are contained, and these are defined by below formulas 8 to 10.

$$y=[y_1, y_2, \ldots, y_n]^T \in \{0,1\} \qquad \text{Formula 8}$$

$$w=[w_0, w_1, w_2]^T \qquad \text{Formula 9}$$

$$x_n=[1, x_1(t), x_2(t)]^T \qquad \text{Formula 10}$$

The evaluation value s is calculated by formula 6, on the basis of the learning parameter w when the likelihood p(y|w) is at the maximum in formula 7 and the vector $x_n$ in which the index values are contained. By using the logistic regression, the evaluation value s for deciding which one of the first candidate signal $R_1(t)$ and the second candidate signal $R_2(t)$ is an appropriate waveform can be calculated on the basis of the distribution of the index value. Although the index values contained in the vector $x_n$ in formula 10 are both of $x_1(t)$ and $x_2(t)$, only one of the index values $x_1(t)$ and $x_2(t)$ may be contained in the vector $x_n$. Also, a multidimensional index value other than frequency and angle change amount may be added to the vector $x_n$. Thereby, the evaluation value s can be decided on the basis of various parameters.

(Evaluation by Neural Network)

The signal deciding unit 133 may calculate the evaluation value s, using a neural network. For example, the signal deciding unit 133 may configure a feedforward neural network of three layers including an input layer for inputting the above index value, an output layer for outputting an output value (a selecting output value) for selecting the first candidate signal $R_1(t)$ and the second candidate signal $R_2(t)$, and an intermediate layer. The intermediate layer may be configured with a plurality of nodes, and may be configured with a plurality of layers as in Deep Learning, for example. Here, in order to decide the evaluation value s by the neural network, the signal deciding unit 133 needs to cause the neural network to learn by a backpropagation method or the like, for example. For example, the signal deciding unit 133 causes the neural network to learn to output an optimal selecting output value, by inputting an index value with a teacher signal into the input layer, and comparing an output selecting output value and the teacher signal, and feeding back an error generated as a result of comparison to the intermediate layer. Thereby, the accuracy of the selecting output value computed in each node of the intermediate layer is improved.

Then, the signal deciding unit 133 decides the evaluation value s, using the neural network that has learned. The signal deciding unit 133 may give each index value to the input layer, and thereafter decide the evaluation value s on the basis of the selecting output value of the first candidate signal $R_1(t)$ and the second candidate signal $R_2(t)$ output from the output layer, for example. For example, the evaluation value s may be a value obtained by converting the selecting output value of the second candidate signal $R_2(t)$ by a sigmoid function. Also, the evaluation value s may be a ratio of the selecting output value of the second candidate signal $R_2(t)$ to the summation of the selecting output values of respective candidate signals. Thereby, the evaluation value s for deciding which one of the first candidate signal $R_1(t)$ and the second candidate signal $R_2(t)$ is an appropriate waveform can be calculated directly from the neural network. Also, by using the neural network, multidimensional index values other than the frequency and the angle change amount are input into the input layer. Thereby, the evaluation value s can be decided on the basis of various parameters.

(Setting of Bias)

Also, the bias may be added in advance in the process for deciding the evaluation value s, so that one of the first candidate signal $R_1(t)$ and the second candidate signal $R_2(t)$ is selected preferentially. For example, when the displacement of the vibration of the respiration is approximately ⅓ to ½ of the wavelength of the radiation wave, both of the first candidate signal $R_1(t)$ and the second candidate signal $R_2(t)$ can express the waveform of the vibration of the respiration with the same degree of accuracy. In this case, it is desirable to use preferentially the second candidate signal $R_2(t)$ that reflects the direction of the vibration of the respiration (inhale direction and exhale direction). Hence, for example, the signal deciding unit 133 may add a bias to give a weight on the second candidate signal $R_2(t)$ at the time of the decision of the evaluation value s. In this case, specifically, the statistical identification model in the logistic regression and the intermediate layer of the neural network may be adjusted in such a manner that a high value is output for the value relevant to the second candidate signal $R_2(t)$ as compared with the value relevant to the first candidate signal $R_1(t)$. Thereby, when both of the first candidate signal $R_1(t)$ and the second candidate signal $R_2(t)$ express the waveform of the vibration of the respiration with the same degree of accuracy, the second candidate signal $R_2(t)$ that reflects the direction of the vibration of the respiration is selected preferentially.

[4-3. Decision of One-Dimensional Signal]

Next, the signal deciding unit 133 executes a process for deciding a one-dimensional signal r(t) to output, on the basis of the evaluation value s (S203). First, the signal deciding unit 133 selects one or both of the first candidate signal $R_1(t)$ and the second candidate signal $R_2(t)$, on the basis of the evaluation value s. Then, the signal deciding unit 133 adjusts the phases of a plurality of candidate signals, as necessary. Then, if the signal deciding unit 133 selects both of the candidate signals in the selection of candidate signal, the signal deciding unit 133 executes a process for merging both of the candidate signals. In the following, a process for deciding the one-dimensional signal r(t) will be described.
(Utilization of Evaluation Value)

The signal deciding unit 133 selects one or both of the first candidate signal $R_1(t)$ and the second candidate signal $R_2(t)$ on the basis of the evaluation value s. For example, the signal deciding unit 133 may decide the first candidate signal $R_1(t)$ as the one-dimensional signal r(t) when the evaluation value s is smaller than a predetermined threshold value, and the second candidate signal $R_2(t)$ as the one-dimensional signal r(t) when the evaluation value s is equal to or larger than the predetermined threshold value. Also, when deciding the one-dimensional signal r(t) by merging both of the candidate signals, the signal deciding unit 133 may use the evaluation value s as a weight for each candidate signal, as described later.

(Adjustment of Phase)

The signal deciding unit 133 needs to adjust the phases of both candidate signals, when selecting one of the candidate signals at the last time as the one-dimensional signal r(t) and thereafter switching it to the other candidate signal, or when merging both candidate signals, for example. For example, the phase $\phi_1$ of the first candidate signal $R_1(t)$ and the phase $\phi_2$ of the second candidate signal $R_2(t)$ do not necessarily match to each other. Hence, the signal deciding unit 133 adjusts the phase of one of the candidate signals to the phase of the other candidate signal. Thereby, the waveform is prevented from being disturbed due to mismatch of the phases of candidate signals in a signal switching process of the one-dimensional signal r(t) and a merging process of the both candidate signals. Note that, in the present embodiment, a process for adjusting the phase of the first candidate signal $R_1(t)$ to the phase of the second candidate signal $R_2(t)$ is performed. In the following, a phase adjusting process will be described.

The signal deciding unit 133 performs normalization for equalizing the amplitudes of candidate signals, before the phase adjusting process. For example, the amplitude of each candidate signal may be calculated from the standard deviation, the difference between the maximum value and the minimum value, the maximum value of the absolute value of the output value of each candidate signal, or the like. Then, the amplitude of each candidate signal may be normalized by linear conversion or the like, on the basis of the calculated amplitude. Also, the amplitude of one of the candidate signals may be adjusted to the amplitude of the other candidate signal. In this case, the signal deciding unit 133 may cut out a signal of longer time than one respiration cycle from each candidate signal, and calculate the amplitude of each candidate signal from the cut signal. For example, a respiration cycle is approximately 3 seconds, and therefore it is preferable to cut out a signal of approximately 3 to 10 seconds. Thereby, the amplitude of each candidate signal is calculated in consideration of the influence of the fluctuation of the amplitude due to the fluctuation of the respiration. Although in the present embodiment the normalization is performed with respect to the amplitudes of the both candidate signals, the normalization of the amplitude is needless to be performed when the influence of the amplitude does not become a problem in post-processing. Although in the present embodiment the signal deciding unit 133 performs normalization, the beat signal acquiring unit 110, the filter unit 120, the first converting unit 131, or the second converting unit 132 may perform normalization with respect to the beat signal D(t), the first candidate signal $R_1(t)$, or the second candidate signal $R_2(t)$. Also, the signal deciding unit 133 may perform a process for setting the normalized amplitude of each candidate signal to its original value.

When the normalization process of each candidate signal is performed, the candidate signals are expressed by below formula 11 and formula 12, respectively.

$$R_1(t)=\cos(2\pi f_{r1}t+\varphi_1) \qquad \text{Formula 11}$$

$$R_2(t)=\cos(2\pi f_{r2}t+\varphi_2) \qquad \text{Formula 12}$$

Here, in the present embodiment, the signal deciding unit 133 executes a process to adjust the phase of the first candidate signal $R_1(t)$ to the phase of the second candidate signal $R_2(t)$, as described above. The signal deciding unit 133 converts the first candidate signal $R_1(t)$ to an analysis signal Ref(t), using Hilbert transformation (formula 13).

$$\text{Ref}(t)=\exp[j(2\pi f_{r1}t+\varphi_1)] \qquad \text{Formula 13}$$

Thereafter, the signal deciding unit 133 multiplies $R_2(t)$ and Ref(t), and extracts a phase difference $\Delta\phi$ (formula 14).

$$Ph(t)=F_{LPF}(R_2(t)\cdot\text{Ref}(t))=\exp[j(2\pi\Delta ft+\Delta\varphi)] \qquad \text{Formula 14}$$

Here, $\Delta f$ is equal to $f_{r1}-f_{r2}$, and $\Delta\phi$ is equal to $\phi_1-\phi_2$, and $F_{LPF}(x)$ is an expression that represents a low-pass filter for reducing the frequency component expressed by $f_{r1}+f_{r2}$. This low-pass filter has a characteristic of steep cutoff, and for example may be a filter that removes a frequency component of 0.1 Hz or more. Thereby, the component of $f_{r1}+f_{r2}$ generated by multiplying $R_2(t)$ and Ref(t) can be removed. Also, $\Delta f$ is the frequency of each candidate signal, and $\Delta f$ can be calculated by Hilbert transformation or the like. However, the frequencies of the candidate signals have similar values, and therefore the signal deciding unit 133 may assume that $\Delta f$ is 0. Thereby, Ph(t) is assumed as a signal indicating the phase difference between the candidate signals (formula 15).

$$Ph(t)=\text{Exp}[j\Delta\varphi] \qquad \text{Formula 15}$$

The signal deciding unit 133 can obtain a complex signal $R_q(t)$ having the frequency component of the first candidate signal $R_1(t)$ and the phase of the second candidate signal $R_2(t)$, by multiplying Ref(t) obtained in advance and the complex conjugate of the above Ph(t), (formula 16). Then, the signal deciding unit 133 can obtain the real part of the complex signal $R_q(t)$ as the first candidate signal $R_{1a}(t)$ having the phase of the second candidate signal $R_2(t)$ (formula 17).

$$Rq(t)=\text{Ref}(t)\cdot Ph(t)=\exp[j(2\pi f_{r1}t+\varphi_2)] \qquad \text{Formula 16}$$

$$R_{1a}(t)=Re[Rq(t)]=\cos(2\pi f_{r1}t+\varphi_2) \qquad \text{Formula 17}$$

By the above phase adjusting process, the signal deciding unit 133 can execute a process in a state in which the phases of the candidate signals are equalized, when switching the candidate signals or when merging the candidate signals. Thereby, a continuous one-dimensional signal r(t) can be output. Note that, when, in order to switch, the phases are adjusted and thereafter the one-dimensional signal r(t) is output for example, it is possible that the waveform including much fluctuation is transformed into a distorted shape. Hence, the signal deciding unit 133 may adjust the phases and thereafter process the phases using exponentially smoothed average or the like in such a manner to change the phases to the above phase gradually, for example. Also, when the phase of one of the candidate signals changes because of adjustment, it is supposed that the waveform of the above candidate signal changes in the time direction. Hence, the signal deciding unit 133 may perform a delay process or the like, to adjust the phase of the above candidate signal to the phase of the other candidate signal, while changing the waveform gradually.

(Merging Process)

When deciding the one-dimensional signal r(t) using the both candidate signals, the signal deciding unit 133 may adjust the phases and then perform a process for merging the both candidate signals. For example, the signal deciding unit 133 can decide the one-dimensional signal r(t), using the evaluation value s as a weight, as in below formula 18.

$$r(t)=(1-s)R_{1a}(t)+sR_2(t) \qquad \text{Formula 18}$$

The one-dimensional signal r(t) indicated by formula 18 is expressed as a weighted sum of the first candidate signal $R_{1a}(t)$ and the second candidate signal $R_2(t)$ whose phases are corrected. Thereby, the signal deciding unit 133 can decide the value of the one-dimensional signal r(t), following the value of the evaluation value s.

By the above process for deciding the one-dimensional signal r(t), a signal that expresses the waveform of the vibration of the respiration more appropriately can be selected from among the first candidate signal $R_1(t)$ and the second candidate signal $R_2(t)$ that fluctuate in response to the displacement of the vibration of the respiration. Thereby, the one-dimensional signal r(t) that reflects the vibration of the respiration more accurately can be output, regardless of the magnitude of the displacement of the vibration of the respiration. Hence, in a cycle estimating process of post-processing, the cycle of the vibration of the respiration that includes fine fluctuation that leads to a large fluctuation of the displacement of the vibration can be estimated more accurately.

<5. Exemplary Operation of Vibration State Estimation Device>

Figure 10:
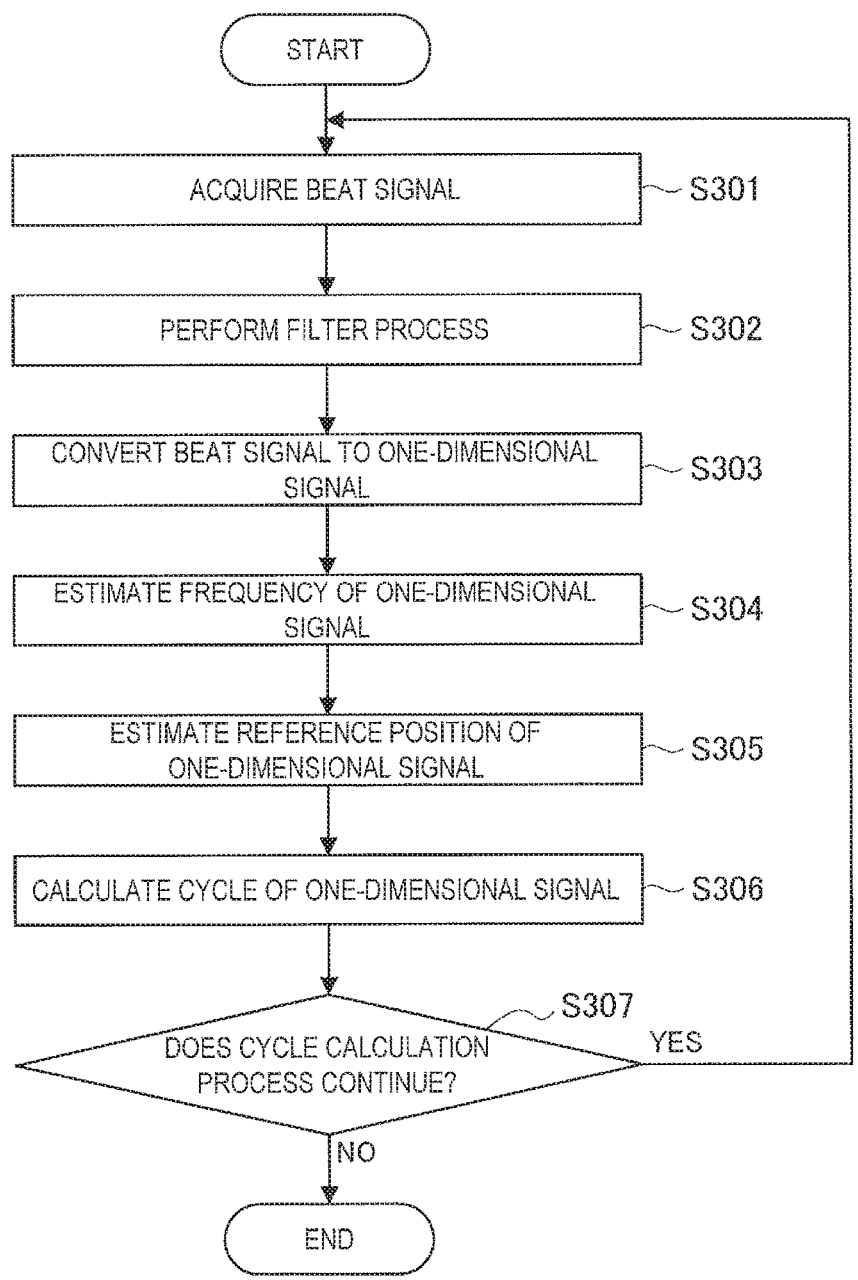
FIG. 10 is a flowchart illustrating an exemplary operation of a vibration state estimation device according to an embodiment of the present invention.

Next, an exemplary operation of the vibration state estimation device 10 according to an embodiment of the present invention will be described. FIG. 10 is a flowchart illustrating the exemplary operation of the vibration state estimation device 10 according to an embodiment of the present invention.

First, the beat signal acquiring unit 110 acquires the beat signal D(t) output from the Doppler sensor 2 (S301). Then, the filter unit 120 executes a filter process to reduce or remove a low-frequency component, such as a direct current component, from the acquired beat signal D(t) (S302).

Thereafter, the signal converting unit 130 converts the filtered beat signal D(t) to the one-dimensional signal r(t) (S303). Then, the frequency estimating unit 140 estimates the frequency of the converted one-dimensional signal r(t), using one or a plurality of means (S304). Thereafter, the reference position estimating unit 150 estimates the reference position of the one-dimensional signal r(t), using the estimated frequency (S305). Then, the cycle calculating unit 160 calculates the cycle of the respiration, from the interval of the reference positions next to each other in the one-dimensional signal r(t) (S306). After calculating the cycle, the vibration state estimation device 10 determines whether or not to calculate the cycle of the vibration continuously, on the basis of whether or not the beat signal D(t) has been acquired, or on the basis of a user's input of the vibration state estimation device 10, for example (S307). If the cycle of the vibration is calculated continuously (YES), the beat signal acquiring process of step S301 is performed repeatedly. On the other hand, if the cycle of the vibration is not calculated (NO), the vibration state estimation device 10 ends the operation.

<6. Exemplary Hardware Configuration>

In the above, the exemplary operation of the vibration state estimation device 10 according to an embodiment of the present invention has been described. The above information processing of the vibration state estimation device 10 is achieved by cooperation between software and the vibration state estimation device 10. In the following, the hardware configuration of the vibration state estimation device 10 according to the embodiment of the present invention will be described.

Figure 11:
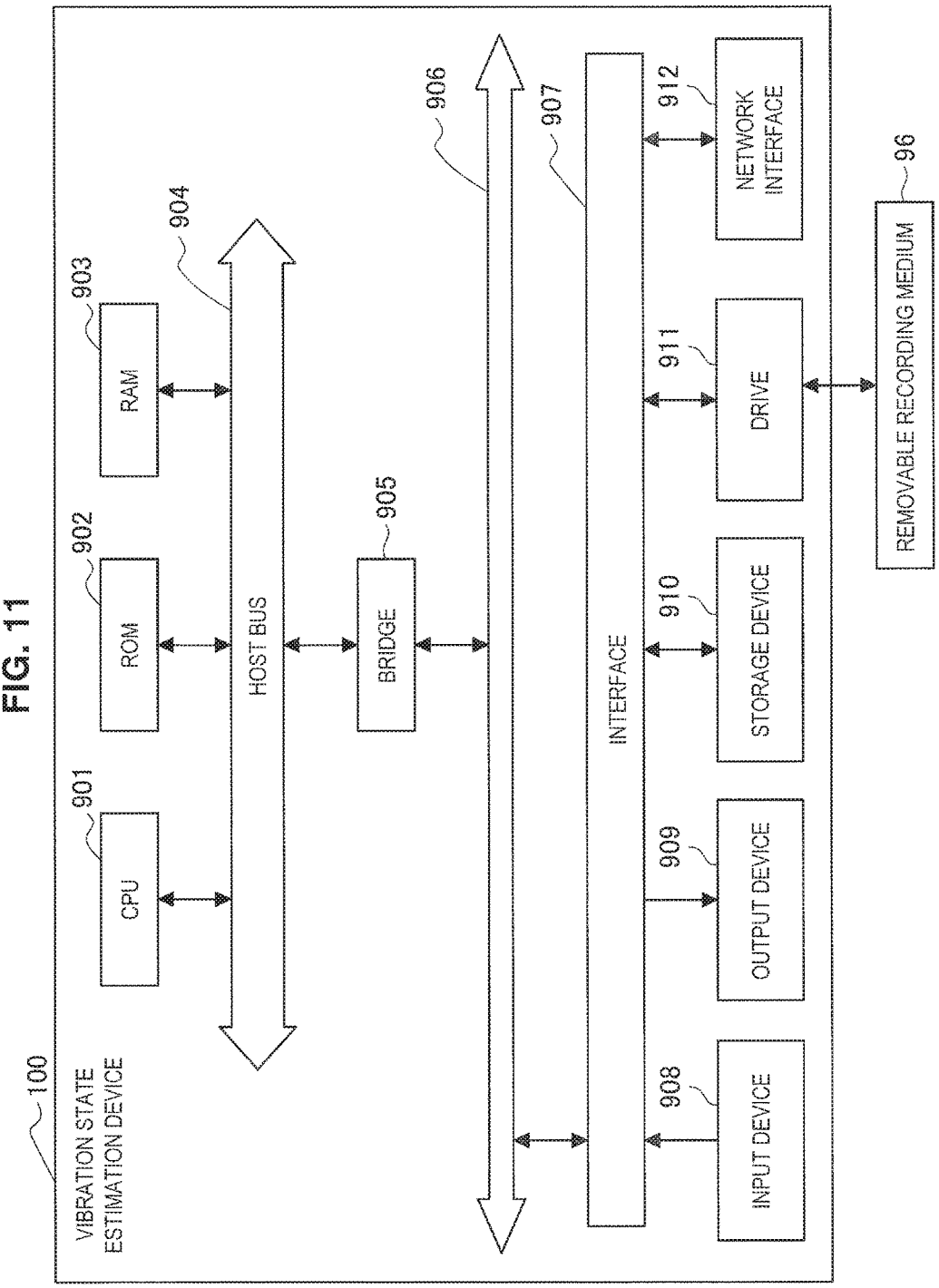
FIG. 11 is a block diagram illustrating an exemplary hardware configuration of a vibration state estimation device according to an embodiment of the present invention.

FIG. 11 is a block diagram illustrating an exemplary hardware configuration of the vibration state estimation device 10 according to the embodiment of the present invention. Referring to FIG. 11, the vibration state estimation device 10 includes a central processing unit (CPU) 901, a read only memory (ROM) 902, a random access memory (RAM) 903, and a host bus 904. Also, the vibration state estimation device 10 includes a bridge 905, an external bus 906, an interface 907, an input device 908, an output device 909, a storage device 910, a drive 911, and a network interface 912.

The CPU 901 functions as an operation processor and a control device, and controls overall operation in the vibration state estimation device 10 in accordance with various types of programs. Also, the CPU 901 may be a microprocessor. Note that the CPU 901 controls the overall operation or a part thereof in the vibration state estimation device 10. For example, the ROM 902 stores programs and calculation parameters used by the CPU 901. The RAM 903 temporarily stores the programs that are used in execution of the CPU 901, and the parameters that changes as appropriate in the execution, etc. These devices are connected to each other by the host bus 904 including a CPU bus.

The host bus 904 is connected to the external bus 906, such as a peripheral component interconnect/interface (PCI) bus, via the bridge 905. Note that, the host bus 904, the bridge 905, and the external bus 906 are needless to be separated from each other, and one bus may have these functions.

The input device 908 includes input means for allowing a user to input information, such as a mouse, a keyboard, a touch panel, a button, a microphone, a switch, and a lever, as well as an input control circuit that generates an input signal on the basis of input by the user and outputs it to the CPU 901, etc. The user of the vibration state estimation device 10 can input various types of data into the vibration state estimation device 10 and instruct a processing operation by handling the input device 908.

The output device 909 includes a display device, such as, a CRT display device, a liquid crystal display (LCD) device, an OLED device, and a lamp, for example. Further, the output device 909 includes an audio output device, such as a speaker and a headphone. The output device 909 outputs reproduced content, for example. Specifically, the display device displays various types of information, such as reproduced video data, with a text or an image On the other hand, the audio output device converts reproduced sound data and text data displayed on the display device to sound and outputs it.

The storage device 910 is a device for data storage in the vibration state estimation device 10 according to the embodiment of the present invention. The storage device 910 may include a storage medium, a recording device for recording data in the storage medium, a read device for reading data from the storage medium, and a deleting device for deleting data stored in the storage medium. The storage device is configured with a hard disc drive (HDD) and a solid state drive (SSD), for example. This storage device 910 contains programs executed by the CPU 901 and various types of data. Note that the storage device 910 realizes the function of a storage unit (not depicted).

The drive 911 is a reader/writer for storage medium, and is incorporated in or attached to the vibration state estimation device 10. The drive 911 reads the information recorded in a removable storage medium 96, such as a magnetic disk, an optical disc, a magneto-optical disk, or a semiconductor memory, which are put inside, and outputs the read information to the RAM 903. Also, the drive 911 can write information into the removable storage medium 96.

The network interface 912 is a communication interface including a communication device or the like for connecting to other devices, for example. Also, the network interface 912 may be a wireless local area network (LAN) compatible communication device, a long term evolution (LTE) compatible communication device, or a Bluetooth communication device. Also, the network interface 912 may be a wire communication device that communicates via wire. Note that the network interface 912 realizes the function of a communication unit (not depicted).

In the above, an example of the hardware configuration of the vibration state estimation device 10 has been illustrated. The above components may be configured with general-purpose components, or may be configured with hardware specialized in the functions of the respective components. Such configurations can be changed as appropriate according to the technology level of the time when they are carried out.

<7. Conclusion>

Heretofore, with reference to FIGS. 1 to 11, an embodiment of the present invention has been described. According to an embodiment of the present invention, the vibration state estimation device 10 converts the acquired beat signal to the one-dimensional candidate signals using a plurality of signal conversion means, and evaluates which one of the converted candidate signals expresses the vibration of the respiration more accurately, and decides the one-dimensional signal to output, on the basis of the evaluation result. Thereby, even when the fluctuation of the vibration of the respiration is large, the one-dimensional signal reflecting the vibration of the respiration more accurately can be extracted. Thus, in the vibration cycle estimation process of post-processing, the cycle of the vibration can be estimated on the basis of the waveform that is close to the vibration of the actual respiration, and therefore the cycle of the vibration can be estimated highly accurately.

Heretofore, preferred embodiments of the present invention have been described in detail with reference to the appended drawings, but the present invention is not limited thereto. It should be understood by those skilled in the art that various changes and alterations may be made without departing from the spirit and scope of the appended claims.

For example, in above the embodiment, the vibration state estimation device 10 acquires the beat signal output from the Doppler sensor 2 in real time, and in parallel performs an analyzing operation, but the present invention is not limited to such an example. For example, the vibration state estimation device according to another embodiment once saves an acquired signal in the storage unit, and takes out the signal repeatedly from the storage unit, when performing the estimation process, in order to perform analysis. Thereby, analysis can be performed for beat signals acquired in the past at a time.

Also, in above the embodiment, a subject is assumed to exist in a sensing area of the Doppler sensor 2, the present invention is not limited to such an example. For example, the Doppler sensor may be installed in such a manner that the Doppler sensor can sense the subject only when the subject exists at a position such as a chair and a bed. Thereby, the subject of analyzing target can be limited. Also, the vibration state estimation device may be a combination of means for sensing presence or absence of the subject and large activity such as walking of the subject. Thereby, the estimation process can be performed only in a limited state, such as when the subject is sleeping.

Also, although in above the embodiment an example in which the vibration of the respiration by a living body is the analyzing target has been described, the present invention is not limited to such an example. For example, the present invention is applicable to various vibration motion, such as heartbeat, pulse, and cramping motion of a living body, as well as vibration of a machine, and back and forth motion of a crank or the like. In this case, the one-dimensional signal including the fine fluctuation of any vibration can be extracted by setting the wavelength of the radiation wave of the Doppler sensor appropriately according to the displacement of the vibration of the analyzing target.

Also, although in above the embodiment the Doppler sensor 2 and the vibration state estimation device 10 constitute the vibration state estimation system 1, the present invention is not limited to such an example. For example, a vibration state estimation device or a vibration state estimation system in which the Doppler sensor 2 and the vibration state estimation device 10 are integrated may be provided.

Also, each step in the process of the vibration state estimation device 10 and the signal converting unit 130 of the present specification is needless to be processed in temporal sequence along the order described in the flowchart necessarily. For example, each step in the process of the vibration state estimation device 10 or the signal converting unit 130 may be processed in an order different from the order describe in the flowchart, or may be processed in parallel.

Also, a computer program for causing the hardware such as the CPU, the ROM and the RAM incorporated in the vibration state estimation device 10 to provide the same function as each configuration of the above the vibration state estimation device 10 can be created. Also, a storage medium that stores the computer program is provided as well.

What is claimed is:

1. An estimation device comprising:
a beat signal acquiring unit acquiring a beat signal from a Doppler sensor, the beat signal based on a motion of an object detected by the Doppler sensor;
a first converting unit configured to convert the beat signal to a one-dimensional first candidate signal on the basis of a two-dimensional distribution of the beat signal, the two dimensions being an in-phase (I) dimension and a quadrature (Q) dimension, and the one-dimensional first candidate signal being generated based on the distribution of the beat signal on an IQ plane;
a second converting unit configured to convert the beat signal to a one-dimensional second candidate signal on the basis of a two-dimensional position change of the beat signal, the one-dimensional second candidate signal generated based on the position change of the beat signal on the IQ plane; and
a signal deciding unit configured to decide a one-dimensional signal on the basis of the first candidate signal and the second candidate signal,
wherein the signal deciding unit decides an evaluation value by comparing a feature value of the first candidate signal and a feature value of the second candidate signal, and selects one or both of the first candidate signal and the second candidate signal as the one-dimensional signal based on the evaluation value.

2. The estimation device according to claim 1, wherein the feature value is a frequency.

3. The estimation device according to claim 1, wherein
a center of the distribution of the beat signal is estimated on the basis of the two-dimensional distribution of the beat signal, and
the signal deciding unit decides an evaluation value on the basis of an amount of change of a rotation angle of the beat signal with respect to the center of the distribution, and selects the first candidate signal and/or the second candidate signal as the one-dimensional signal on the basis of the evaluation value.

4. The estimation device according to claim 1, wherein
when selecting both of the first candidate signal and the second candidate signal as the one-dimensional signal, the signal deciding unit decides the one-dimensional signal by weighting the first candidate signal and the second candidate signal on the basis of the evaluation value.

5. The estimation device according to claim 1, wherein
when the signal deciding unit selects one of the first candidate signal and the second candidate signal, and then selects the other of the first candidate signal and the second candidate signal, the signal deciding unit adjusts a phase of the one of the first candidate signal and the second candidate signal to a phase of the other of the first candidate signal and the second candidate signal.

6. The estimation device according to claim 1, wherein
when selecting both of the first candidate signal and the second candidate signal, the signal deciding unit adjusts a phase of one of the first candidate signal and the second candidate signal to a phase of the other of the first candidate signal and the second candidate signal.

7. The estimation device according to claim 1, wherein
the first converting unit calculates an inner product of a two-dimensional vector expressing the beat signal and an eigenvector corresponding to a maximum eigenvalue of a covariance matrix of the beat signal, and
a result of the calculation corresponds to the first candidate signal.

8. The estimation device according to claim 1, wherein
a center of the distribution of the beat signal is estimated on the basis of the two-dimensional distribution of the beat signal, and
the second converting unit multiplies a distance from the center of the distribution to a position of the beat signal, by an amount of change of a rotation angle of the beat signal with respect to the center of the distribution, and
a result of the multiplication corresponds to the second candidate signal.

9. The estimation device according to claim 1, further comprising:
a frequency estimating unit configured to estimate a frequency of the one-dimensional signal;
a reference position estimating unit configured to estimate a plurality of reference positions of the one-dimensional signal on the basis of the frequency, and
a cycle calculating unit configured to calculate a cycle of the one-dimensional signal; wherein the cycle of the one-dimensional signal is an interval between one reference position and another reference position estimated by the reference position estimating unit, and
the one reference position and the other reference position are continuous.

10. The estimation device according to claim 1, wherein
the beat signal is a beat signal detected by a Doppler sensor in response to vibration caused by respiration of a living body.

11. An estimation method comprising:
a beat-acquiring step for acquiring a beat signal from a Doppler sensor, the beat signal based on a motion of an object detected by the Doppler sensor;
a first conversion step for converting the beat signal to a one-dimensional first candidate signal on the basis of a two-dimensional distribution of the beat signal, the two dimensions being an in-phase (I) dimension and a quadrature (Q) dimension, and the one-dimensional first candidate signal being generated based on the distribution of the beat signal on an IQ plane;
a second conversion step for converting the beat signal to a one-dimensional second candidate signal on the basis of a two-dimensional position change of the beat signal, the one-dimensional second candidate signal generated based on the position change of the beat signal on the IQ plane; and
a decision step for deciding a one-dimensional signal on the basis of the first candidate signal and the second candidate signal,
wherein the decision step includes deciding an evaluation value by comparing a feature value of the first candidate signal and a feature value of the second candidate signal, and selecting one or both of the first candidate signal and the second candidate signal as the one-dimensional signal based on the evaluation value.

12. A non-transitory computer readable recording medium comprising instructions for execution by a control portion of an estimation device, the instructions including:
acquiring a beat signal from a Doppler sensor, the beat signal based on a motion of an object detected by the Doppler sensor;
converting the beat signal to a one-dimensional first candidate signal on the basis of a two-dimensional distribution of the beat signal, the two dimensions being an in-phase (I) dimension and a quadrature (Q) dimension, and the one-dimensional first candidate signal being generated based on the distribution of the beat signal on an IQ plane;
converting the beat signal to a one-dimensional second candidate signal on the basis of a two-dimensional position change of the beat signal, the one-dimensional second candidate signal generated based on the position change of the beat signal on the IQ plane; and
deciding a one-dimensional signal on the basis of the first candidate signal and the second candidate signal,
wherein deciding the one-dimensional signal includes deciding an evaluation value by comparing a feature value of the first candidate signal and a feature value of the second candidate signal, and selecting one or both of the first candidate signal and the second candidate signal as the one-dimensional signal based on the evaluation value.

* * * * *